United States Patent
Haider et al.

(10) Patent No.: US 11,116,900 B2
(45) Date of Patent: *Sep. 14, 2021

(54) CONTINUOUS GLUCOSE MONITORING INJECTION DEVICE

(71) Applicant: Becton, Dickinson and Company, Franklin Lakes, NJ (US)

(72) Inventors: M. Ishaq Haider, Cary, NC (US); Noel Harvey, Efland, NC (US); Sundeep Kankanala, Bloomington, IN (US); Frank Martin, Durham, NC (US); Ronald Pettis, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/377,048

(22) Filed: Apr. 5, 2019

(65) Prior Publication Data
US 2019/0298920 A1 Oct. 3, 2019

Related U.S. Application Data

(63) Continuation of application No. 15/500,913, filed as application No. PCT/US2015/043005 on Jul. 30, 2015, now Pat. No. 10,252,002.
(Continued)

(51) Int. Cl.
*A61M 5/172* (2006.01)
*G16H 15/00* (2018.01)
(Continued)

(52) U.S. Cl.
CPC ...... *A61M 5/1723* (2013.01); *A61M 5/14244* (2013.01); *A61M 5/14248* (2013.01);
(Continued)

(58) Field of Classification Search
CPC ............ A61M 5/1723; A61M 5/14244; A61M 5/14248; A61M 5/172; A61B 5/14532; A61B 5/4839; G16H 20/17; G16H 40/63
See application file for complete search history.

(56) References Cited

U.S. PATENT DOCUMENTS

2007/0066938 A1   3/2007   Iio
2008/0306434 A1   12/2008   Dobbles
(Continued)

FOREIGN PATENT DOCUMENTS

JP   2007/111518 A   5/2007
WO   WO 2010/146579 A1   12/2010

OTHER PUBLICATIONS

Supplementary Extended Search Report dated Feb. 23, 2018 for EP 15826590.0, filed Feb. 10, 2017.
(Continued)

*Primary Examiner* — Manuel A Mendez
(74) *Attorney, Agent, or Firm* — Knobbe Martens Olson & Bear, LLP

(57) ABSTRACT

An electronic insulin delivery device receives glucose data from a glucose monitor and sets a bolus dose amount. The device may take the form of an insulin pen with automatic priming and accurate dosing provided by a motor in connection with an encoder. The device may communicate with and be controlled by a smart phone device. The smart phone device provides a user interface to receive user data including patient weight, insulin to carbohydrate ratio and exercise factor, and to send instructions to the device, including dose amount. The dose amount is determined taking into account glucose level and trend, and other factors. The delivery device may be in continuous communication with the glucose monitor and smart phone to provide for near real-time adjustments in glucose treatment. Glucose data, insulin (Continued)

injection data, and other relevant data may be stored and accessible to interested parties.

31 Claims, 17 Drawing Sheets

Related U.S. Application Data

(60) Provisional application No. 62/032,318, filed on Aug. 1, 2014.

(51) Int. Cl.
    *A61M 5/24*     (2006.01)
    *A61M 5/142*     (2006.01)
    *G16H 50/20*     (2018.01)
    *G16H 40/67*     (2018.01)
    *G16H 40/63*     (2018.01)
    *G16H 20/17*     (2018.01)
    *G16H 20/10*     (2018.01)
    *G16H 20/13*     (2018.01)
    *A61M 5/315*     (2006.01)
    *A61M 5/14*     (2006.01)

(52) U.S. Cl.
    CPC .............. *A61M 5/24* (2013.01); *G16H 15/00* (2018.01); *G16H 20/10* (2018.01); *G16H 20/13* (2018.01); *G16H 20/17* (2018.01); *G16H 40/63* (2018.01); *G16H 40/67* (2018.01); *G16H 50/20* (2018.01); *A61M 2005/1402* (2013.01); *A61M 2005/31588* (2013.01); *A61M 2205/3306* (2013.01); *A61M 2205/3368* (2013.01); *A61M 2205/3553* (2013.01); *A61M 2205/3561* (2013.01); *A61M 2205/3584* (2013.01); *A61M 2205/3592* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2230/005* (2013.01); *A61M 2230/201* (2013.01); *A61M 2230/63* (2013.01)

(56) References Cited

U.S. PATENT DOCUMENTS

2011/0098637 A1    4/2011  Hill
2011/0124996 A1*  5/2011  Reinke .................. G16H 15/00
                                              600/365
2012/0245447 A1*  9/2012  Karan .................... G16H 40/63
                                              600/365

OTHER PUBLICATIONS

International Search Report and Written Opinion dated Oct. 23, 2015 for PCT/US2015/043005, filed Jul. 30, 2015.

* cited by examiner

CONTINUOUS GLUCOSE MONITORING INJECTION DEVICE

INCORPORATION BY REFERENCE TO ANY PRIORITY APPLICATIONS

This Application is a continuation of U.S. application Ser. No. 15/500,913, entitled CONTINUOUS GLUCOSE MONITORING INJECTION DEVICE and filed on Jan. 31, 2017, which is a U.S. National Phase Application of PCT International Application No. PCT/US2015/043005, entitled "CONTINUOUS GLUCOSE MONITORING INJECTION DEVICE" and filed on Jul. 30, 2015, which claims priority to U.S. Provisional Application No. 62/032,318, entitled "CONTINUOUS GLUCOSE MONITORING SMART BOLUS PUMP" and filed on Aug. 1, 2014, each of which are incorporated by reference in their entirety.

BACKGROUND

Field

The present invention relates generally to an intelligent injection device. More specifically, the present invention relates to an insulin injector with intelligence and communication capabilities that is capable of providing optimized bolus doses of insulin based on information received from a glucose sensor. Embodiments also relate to injectors that communicate data within a health system to provide information to interested parties including the patient and their healthcare provider.

Description of the Related Art

Diabetes is a group of diseases marked by high levels of blood glucose resulting from defects in insulin production, insulin action, or both. Diabetes can lead to serious complications and premature death, but there are well-known products available for patients with diabetes to help control the disease and lower the risk of complications.

Treatment options for diabetics include specialized diets, oral medications and/or insulin therapy. The primary goal for diabetes treatment is to control a diabetic's blood glucose level in order to increase the chances of a complication-free life. Because of the nature of diabetes and its short-term and long-term complications, it is important that diabetics have a constant awareness of the level of glucose in their blood. For patients who take insulin therapy, it is important to administer insulin in a manner that maintains glucose level, and accommodates the tendency of glucose concentration in the blood to fluctuate as a result of meals and other activities.

Diabetics' bodies have difficulty regulating the production of insulin to manage glucose concentration in their blood. Accordingly, a primary goal of insulin therapy is to help the patient maintain a healthy glucose concentration. Two main components of insulin therapy are measuring glucose level, and delivering insulin as needed. Some diabetics use finger sticks to draw blood samples and test for glucose level, and multiple daily injections (MDI) of insulin. This type of therapy is relatively simple, but requires multiple daily finger sticks and needle injections, which are inconvenient and painful. In addition, the control of glucose is relatively crude, since glucose is measured only episodically, and insulin is delivered episodically with each injection.

Insulin pens typically provide the ability to set a dose. Accordingly, a patient can determine how much insulin they need and set the appropriate dose, and then use the pen device to deliver that dose. This system, however, requires a higher level of sophistication and involvement on the part of the patient.

At a more sophisticated level, other diabetics use insulin pumps to deliver a basal rate of insulin continuously. Insulin pumps may also provide bolus doses of insulin as needed. Insulin pumps are an improvement because they deliver insulin continuously, rather than episodically. They typically include a refillable or replaceable insulin reservoir. They also avoid most of the needle sticks associated with MDI. However, pumps have disadvantages because they can be inconvenient for the user to wear, and require tubing connected to an insertion set at the injection site. They are also expensive since they require electronics and an accurate pump mechanism.

Patch pumps are an insulin delivery device that generally falls between MDI and sophisticated insulin pumps. Patch pumps are typically disposable devices that stick to the patient's skin, and include an insulin reservoir, and a cannula insertion mechanism. Patch pumps may have, but do not require, electronics. They typically include a reservoir of insulin containing a three day supply of insulin for delivery to the patient. Patch pumps may provide a basal rate of insulin, either electronically or mechanically metered, and may also optionally provide bolus doses. There are some patch pumps that deliver only bolus doses. Patch pumps are typically disposable after their roughly three days of use, but some patch pumps may include both durable and disposable components.

There are typically two methods for measuring a user's blood glucose level. One method uses an electronic blood glucose meter wherein a sample of blood is obtained by piercing the skin of a user with a lancet. The sample of blood is then placed on a chemically-active test-strip, which interfaces with the blood glucose meter. Within several seconds of inserting the test-strip into the blood glucose meter, the blood glucose level of the user is read and shown on the digital display of the blood glucose meter.

The blood glucose meter method provides an accurate snapshot of a user's blood glucose level at a single moment in time. However, the blood glucose meter method does not indicate whether the user's glucose level is rising, falling, or steady. Additionally, the blood glucose meter method fails to capture a user's changing blood sugar levels after meals, between meals, and during the night.

Insulin delivery devices and glucose sensors may be combined to provide better therapy. An idealized "artificial pancreas" system would continuously measure glucose levels, and continuously communicate with an insulin delivery device to continuously deliver appropriate amounts of insulin through feedback and determinations. Such a system would also preferably capture glucose measurement and insulin delivery data and provide such information to the patient and their healthcare provider. However, the "artificial pancreas" concept requires expensive equipment, and requires the user to wear an insulin pump with an insertion set and related tubing, which many find inconvenient. While daily injections of insulin are effective for many, daily injections could be improved with adjustable dosing and dosing based on real time or near real time data. However, the currently exist no systems in which there is an interaction between monitored glucose levels, injections of insulin, and the recording of daily events.

SUMMARY

Exemplary embodiments of the present invention address some or all of the above problems and/or disadvantages and provide at least the advantages described below.

According to one embodiment of the present invention, an electronic insulin delivery device for administering a bolus of insulin to a patient is provided. The electronic insulin delivery device includes a receiver configured to receive patient glucose information from an electronic glucose monitor, a processor configured to read the received patient glucose information and determine an appropriate insulin bolus dose for the patient, a dose setting mechanism configured to set an insulin delivery amount corresponding to the determined insulin bolus dose, and a housing having at least one user interface button corresponding to a dispense function for dispensing the determined insulin bolus dose.

According to another embodiment of the present invention, a method in an electronic insulin delivery device for administering insulin to a patient is provided. The method includes receiving glucose information from a glucose monitor, receiving additional patient information from an electronic device via a wireless communication interface, setting an insulin bolus dosage amount based on the glucose information and the additional patient information, and activating a user interface on the electronic insulin delivery device to display the insulin bolus dosage amount.

According to another embodiment of the present invention, an electronic insulin delivery device for administering a bolus of insulin to a patient is provided. The electronic insulin delivery device includes a receiver wirelessly configured to wirelessly connect to an electronic glucose monitor and an electronic device, the receiver configured to receive patient glucose information from the electronic glucose monitor and additional patient information from the electronic device. The delivery device further includes a processor configured to read the received patient glucose information and the additional patient information, determine a patient status based on the received patient glucose information and additional patient information, determine if a notification should be actuated, and actuate a notification.

BRIEF DESCRIPTION OF THE DRAWINGS

The various objects, advantages and novel features of the exemplary embodiments of the present invention will be more readily appreciated from the following detailed description when read in conjunction with the appended drawings, in which.

Throughout the drawing figures, like reference numbers will be understood to refer to like elements, features and structures.

DETAILED DESCRIPTION

Exemplary embodiments of the invention will now be described in connection with the attached drawing figures. One exemplary embodiment of the invention is a smart bolus delivery system, for example, used as an insulin delivery device. The smart bolus delivery system may be integrated with a glucose sensor, a controller, a fitness tracker, and a cloud-based platform to improve therapy and provide data management. It should be understood that the following examples are described in connection with diabetes case, but the invention is not limited to diabetes care. For diabetes care, an exemplary system combines the accuracy and smart functions of an ambulatory insulin pump with the convenience and simplicity of a smart insulin pen to provide a 'near' closed loop control of insulin or other medicament that may have a regulating effect on the disease to improve patient medication adherence and treatment outcome. The exemplary medicament delivery system provides basic injection needs, that is, safety combined with complex dose determinations, and interaction means between patients, healthcare providers and payers. To achieve a 'near' closed loop control, an insulin delivery device can be configured to connect and communicate with one or more external devices that receive or monitor information affecting insulin dosage or that determine insulin dosage requirements.

In one embodiment, the insulin delivery device can process data from the external devices to determine a current status of a user. The insulin device may notify a user of various conditions or events in response to the determined status. In some embodiments the insulin device may be in continuous or near-continuous communication with one or more of the external devices. In other embodiments, the insulin device may communicate with, or receive data from, one or more external devices regularly, semi-regularly, or intermittently. As used herein, the term "regularly" means on a predetermined schedule. For example, the insulin device may receive data from other devices every 0.5, 1, 2, 5, 10, 15 or 30 minutes in some embodiments. The insulin device may be connected to one or more external devices using wireless protocols such as WiFi and Bluetooth. The insulin device can also continuously or near-continuously process data received from one or more external devices to determine a status of the user and notify the user to various conditions or events. In some embodiments, data is processed regularly, semi-regularly, or intermittently. Frequent communication of data between the external devices and the insulin device and the processing of data based on current information and historical information can allow for user notification and changes in insulin dosage based on real-time or near real-time activity and meal composition data.

Figure 1A:
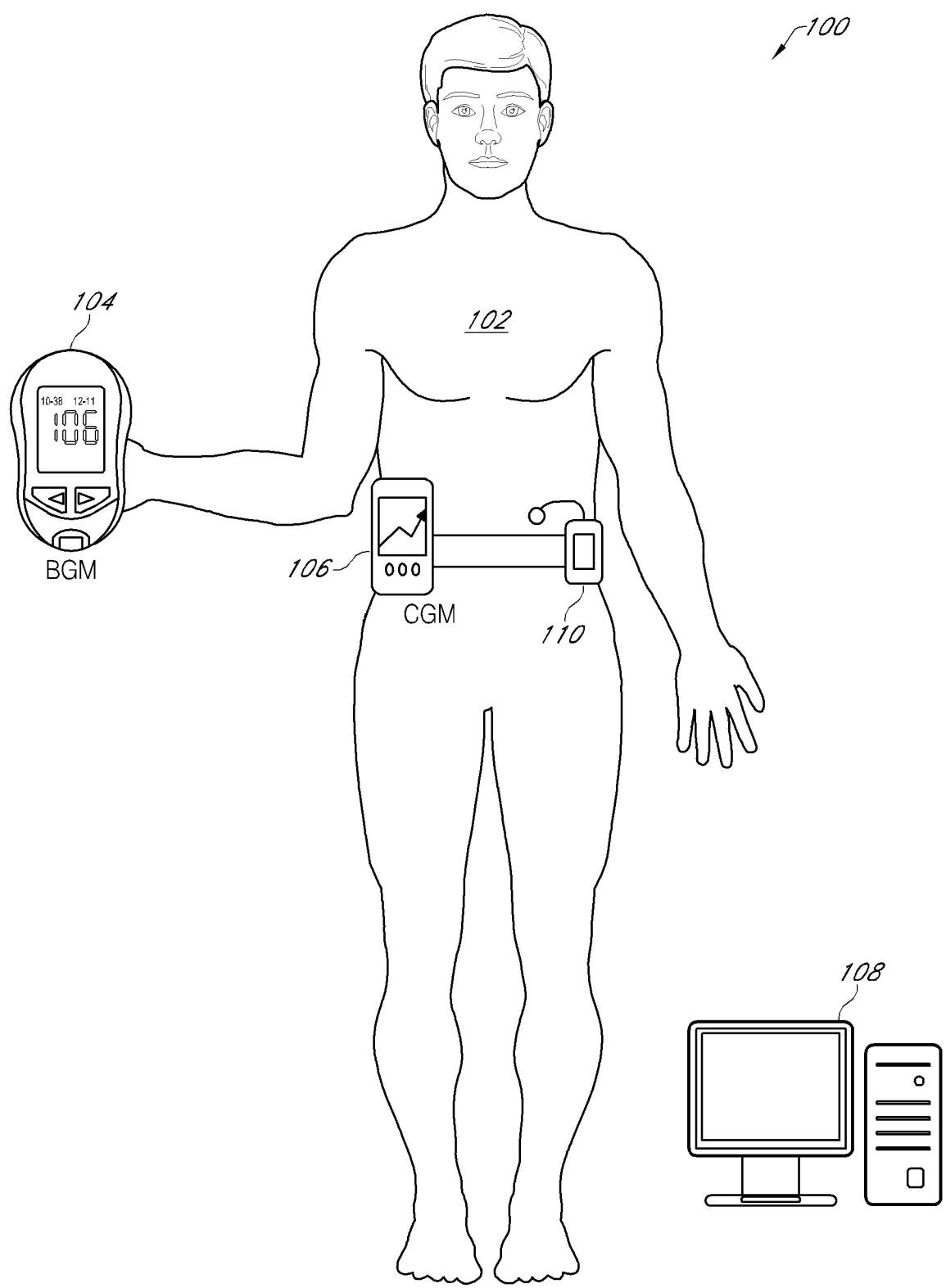
FIG. 1A is a system diagram of an example of a system for delivering medicament to a patient.
Figure 1B:
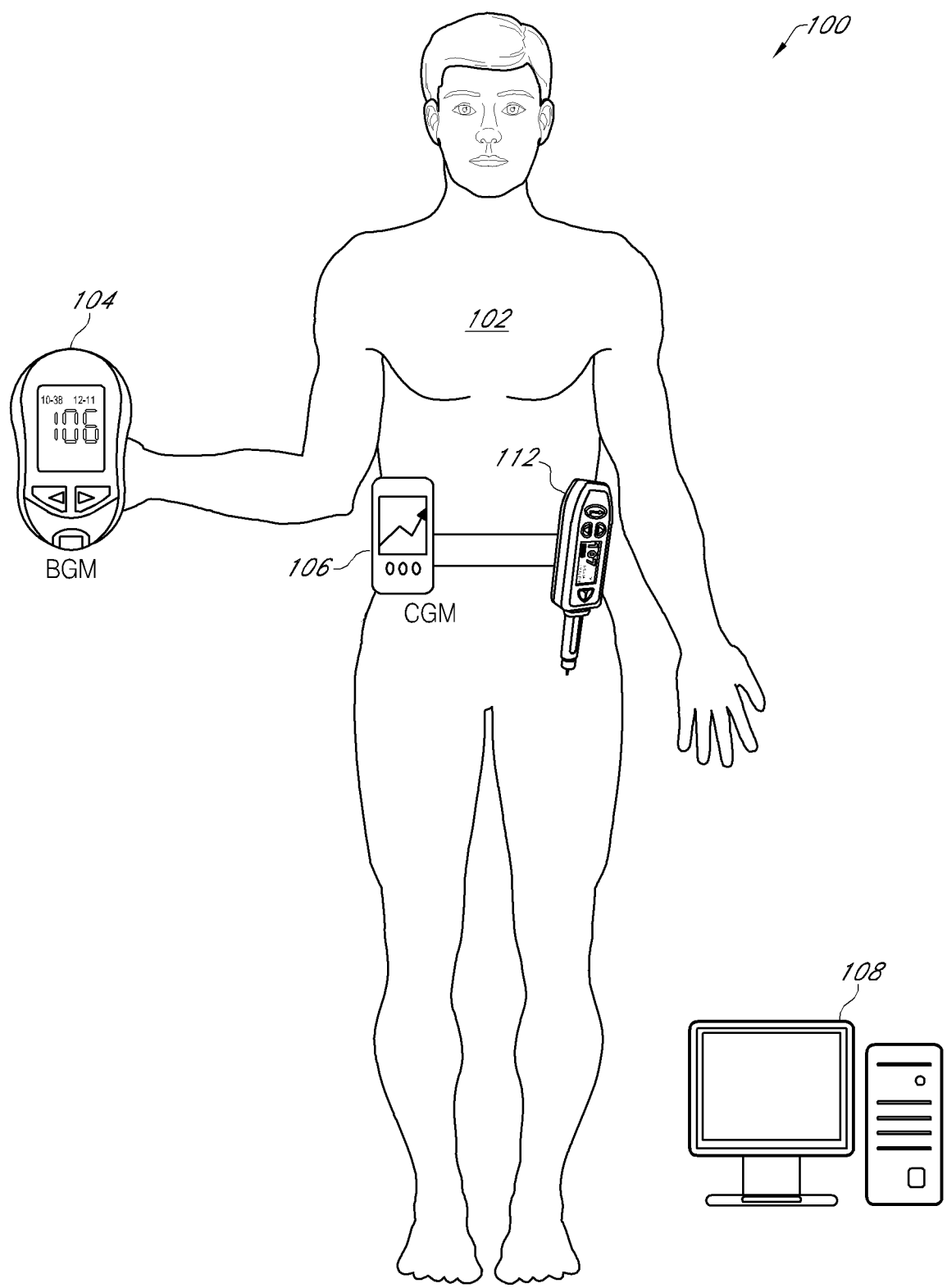
FIG. 1B is a system diagram of a system for delivering medicament to a patient in accordance with an illustrative embodiment.

FIGS. 1A and 1B illustrate an artificial pancreas system, and how a smart bolus injector in the form of an electronic insulin delivery device or intelligent insulin pen can replace a conventional insulin pump in such a system to provide benefits which will be described below. The artificial pancreas system 100 is utilized by a patient 102, and includes a blood glucose monitoring (BGM) device 104, a continuous glucose monitor (CGM) 106, and a computing device 108 to execute one or more processes. The computing device 108 is illustrated as a standalone personal computer. However, it should be understood that any suitable device capable of executing the requisite processes, receiving the requisite inputs, and transmitting control signals and data to necessary devices will suffice. In particular, smart phones may perform the function of the computing device 108 in this system.

In the artificial pancreas system, the CGM provides continuous blood glucose concentration measurement data to the computing device 108. The BGM device is preferably used to calibrate the CGM 106 device. In FIG. 1A, an insulin pump 110 transmits insulin infusion data to the computing device 108. The computing device 108 executes a process that preferably accounts for CGM concentration and trend data received from the CGM 106, insulin infusion data received from the insulin pump 110, and any other relevant data, including food intake data, and computes adjustments to the insulin infusion rate necessary to optimize healthy glucose levels in the patient. The infusion rate adjustments are transmitted to the insulin pump 110 and implemented by the insulin pump 110.

In one exemplary embodiment as depicted in FIG. 1B, the insulin pump 110 is replaced by a smart bolus injector 112. The smart bolus injector 112 may be in the form of an electronic insulin pen with additional features. First, the smart bolus injector 112 is capable of receiving an instruction from the computing device 108 in order to set a dose amount. Second, the smart bolus injector 112 is capable of automatically priming the injector and delivering a bolus dose corresponding to the instruction received from the computing device. It should be understood that the computing device 108 may be a separate component, such as a personal computer or smart phone, but the computing device may also be incorporated into the smart bolus injector 112. The smart bolus injector 112 can include components to receive data from external devices, such as the CGM 106 and the computing device 108.

In accordance with an illustrative embodiment, the smart bolus injector 112 is in continuous, near continuous, or regular communication with the CGM 106, and may be in continuous, or nearly continuous, communication with the computing device 108 and the BGM device 104. In some embodiments, the smart bolus injector 112 can communicate with other external devices that measure or receive dosage relevant information, such as physical activity information, sleep information, diet information, weight information, and other useful information. In some embodiments, the dosage relevant information can be entered directly into the computing device 108. In some embodiments, the dosage relevant information can be received from one or more monitoring devices, such as, for example, a physical activity monitoring device, a sleep monitoring device, a diet monitoring device, and a scale. In some embodiments, one or more of physical activity information and sleep information are monitored by a wearable device. A physical activity monitor can measure data including distance traveled, distance climbed, calories expended, and duration of time at a particular activity level. A sleep monitor can measure data including sleep efficiency, sleep movement, and number of interruptions during a sleep cycle.

The smart bolus injector 112, in some embodiments, may incorporate a blood glucose monitor, but preferably also includes components to receive external data. For example, a user interface can be provided in the smart bolus injector 112 allowing for input of data from a user. The smart bolus injector 112 can also include components to continuously, or near continuously, receive data from and communicate data to a separate device over a network, such as from cloud storage for example. The smart bolus injector can also include components to receive data from and communicate data to a separate device through a wired connection. Advantageously, such an exemplary system provides most of the advantages of a full artificial pancreas system, without the user inconvenience of wearing an insulin pump and insertion set.

Figure 1C:
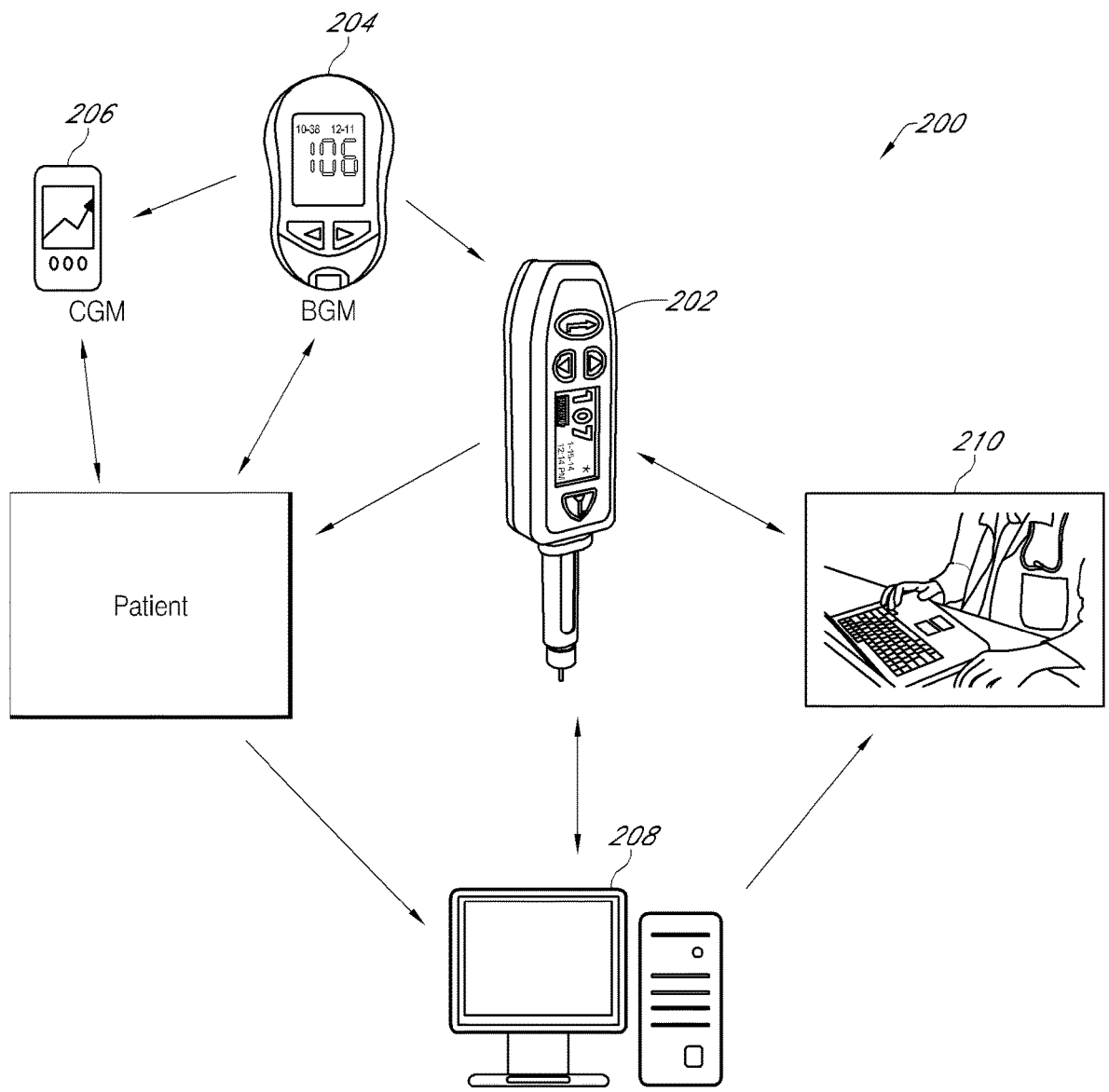
FIG. 1C is a system diagram of a system for delivering medicament to a patient in accordance with an illustrative embodiment.

Another exemplary embodiment is described below in connection with FIG. 1C. This system 200 includes a smart insulin pen 202 that is preferably equipped with a user interface such as the one illustrated in FIG. 3E, a BGM 204 or a CGM 206, a computing device 208 and a health management access point 210. In some embodiments, a BGM 204 is used, while in some alternative embodiments, a CGM 206 is used to more closely achieve the capabilities of an artificial pancreas system. In either case, the insulin pen 202 is equipped with a communication interface, preferably a wireless communication interface. The insulin pen 202 continuously, or near continuously, receives data from the BGM 204 or CGM 206 via the communication interface. The insulin pen 202 also receives data from the computing device 208. In some embodiments, the insulin pen 202 receives data from one or more other external devices that measure dosage relevant information, such as a physical activity monitoring device, a sleep monitoring device, a diet monitoring device, and a scale. The data received from the computing device may be used with a process for determining an insulin dose based on glucose concentration data received from the BGM 204 or CGM 206, as well as any other relevant data.

The computing device may transfer instructions to execute a process to the insulin pen 202 for execution in the insulin pen 202. Alternatively, the process may be executed on the computing device 208 and the required dose information can be transferred to the insulin pen 202. The insulin pen 202 includes a controller that controls a dose setting mechanism within the insulin pen 202. The controller receives dose information determined with a patient specific process and sets the dose accordingly. Advantageously, the process may be adjusted or updated by a third party, such as a healthcare provider, via the health management access point 210. As illustrated, the health management access point 210 includes a bi-directional communication interface. In this manner, healthcare providers can access patient information including up to date records related to the patient's glucose concentration records, insulin injection records, and a current patient specific process. The healthcare provider can similarly send adjustments to the patient specific process to modify the insulin regimen to better control glucose. The patient specific process may be updated by the healthcare provider sending an updated patient specific process to the computing device 208 from the health management access point 210. The insulin pen 202 and/or the computing device 208 may send data to the health management access point 210 that includes time stamped blood glucose concentration records from the BGM 204 or CGM 206, insulin injection data from the insulin pen 202, and any other relevant data captured by the system 200. In one embodiment, the insulin pen 202 and/or the computing device 208 are in continuous, near continuous, or regular communication with the health management access point 210. In one embodiment, the insulin pen 202 makes use of a user interface as illustrated in FIG. 3E and retrieves the patient specific process from the computing device 208, and then determines a required dose based on available data. The controller then sets the required dose automatically. The insulin pen preferably includes audible, tactile, or other means to notify the patient of successful or unsuccessful injections, and records the results for future use in the process. The insulin pen preferably transfers injection data to the health management access point 210. The insulin pen also preferably incorporates certain features of a bolus injector, including delivering real-time glucose information, alerting to high or low glucose readings or failed injections, and providing glucose trend information such that patients may advantageously make more informed decisions to better control their disease.

Figure 2:
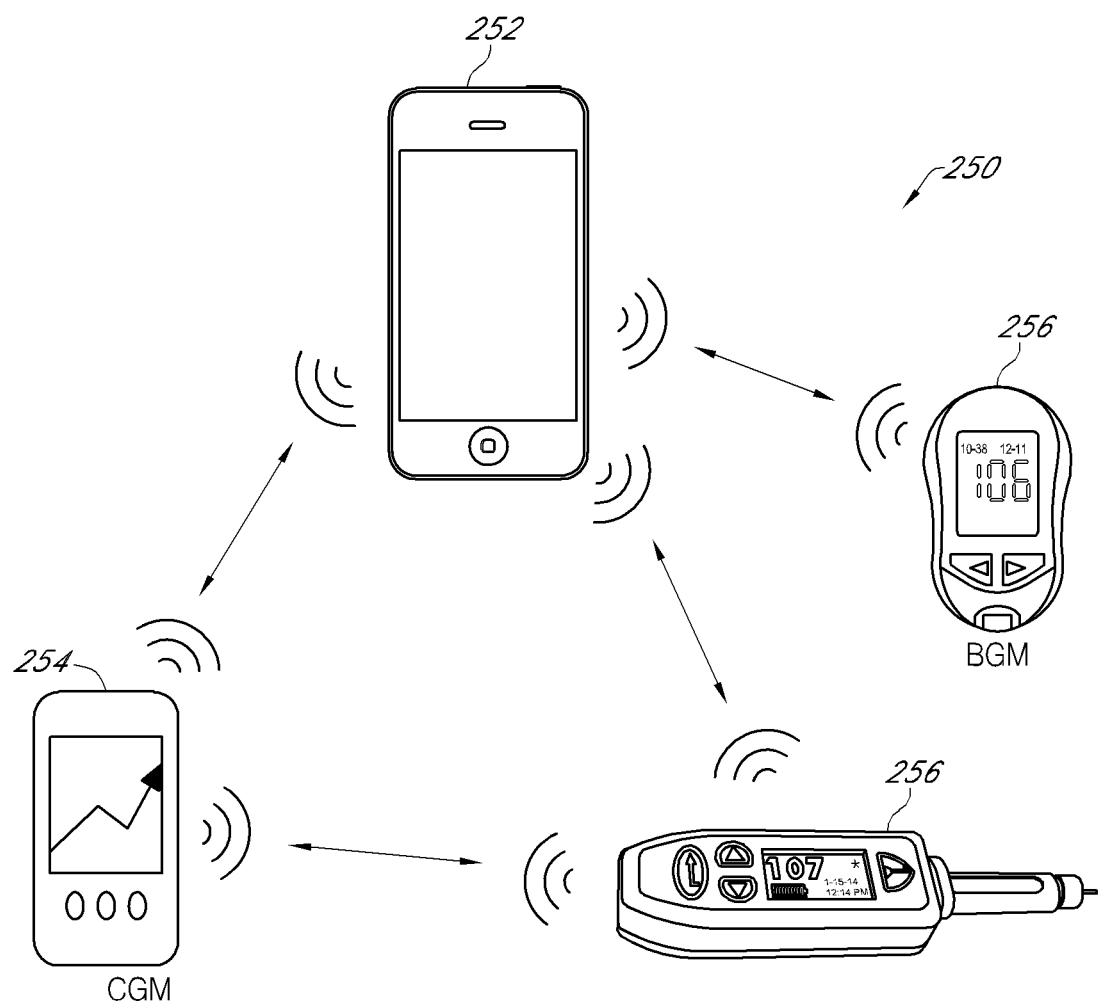
FIG. 2 illustrates components of a wireless system according to an embodiment of the present invention.

FIG. 2 illustrates another system according to an embodiment of the present invention. The system 250 includes a smart phone 252, a CGM 254 and a smart pen injection device 256. The injection device 256 communicates wirelessly with the CGM 254 and/or the smart phone 252. The wireless connections may utilize any suitable wireless protocol including without limitation IEEE 802.11 WiFi, Bluetooth or Zigbee. The injection device 256 may include an encoder and mechanical drive powered by a 12 mm gear motor to drive the plunger in a controlled fashion to deliver accurate doses of insulin. Flow precision is improved by the use of encoders to drive the plunger in a controlled fashion. In one embodiment, the mechanical drive is capable of delivering 30 units of insulin in 5 seconds, and can generate at least 80 psi pressure in the insulin cartridge, and utilizing a 100:1 gear ratio, 120 psi can be achieved. As discussed above, system 250 includes wireless connectivity between the smart pen injection device 256 and the CGM 254 and the smart phone 252. In some embodiments, one or more of the injection device 256 and the smartphone 252 can connect to and communicate with other external devices that measure or receive dosage relevant information, such as physical activity information, sleep information, diet information, weight information, and other medicine used information. In some embodiments, the dosage relevant information can be input into the smartphone 252. In some embodiments, the dosage relevant information can be received from one or more monitoring devices such as for example, a physical activity monitoring device, a sleep monitoring device, a diet monitoring device, and a scale. The injection device 256 may regularly communicate with one or more of the CGM 254, the smart phone 252, and the other external devices. The injection device can also be in continuous, near continuous, intermittent, or semi-regular data communication with one or more of the CGM 254, the smart phone 252, and the other external devices. The system 250 also preferably includes a secured data recording and managing system that is accessible to the patient, authorized healthcare managers and payers or insurers. The system 250 also may include a BGM device 258 that is wirelessly connected to the smart phone 252. The BGM 258 may alternately be embedded and hardwired into the injection device 256. In some embodiments, the smart phone 252 can determine insulin dose requirements, both basal and bolus, based on the patient's physiological information, including glucose concentration measurements and history. The injection device 256 can also include computing capabilities for determining insulin dose requirements. The injection device 256 performs priming and bolus injection, based on a dose amount determined and transmitted to a controller in the smart pen injection device 256. One or more of the smart phone 252 and the injection device 256 can also perform data recording of glucose monitoring data received from the CGM 254, and insulin injections performed by the injection device 256. In some embodiments, the injection device 256 can include a memory for storing data.

In some embodiments, the injection device 256 can process data received from one or more of the CGM 254, the smart phone 252 and the other external devices to determine a status of a user. For example, the injection device 256 can determine high or low glucose readings, the requirement of an insulin dose, an insulin dosage amount, or the requirement of emergency medical treatment. Determinations may be based on both current and historical trend data. The injection device 256 may process data regularly, semi-regularly, continuously, near continuously, or intermittently. In some embodiments, data is processed in real-time or near real-time. The injection device 256 can also notify a user of various conditions and events in response to the status determinations. The injection device 256 may be configured to provide tactile, visual, or auditory notifications to the user. For example, the injection device 256 may display a notification on a user interface of the injection device 256. The user interface may display a current glucose level, a notification that the glucose level is high or low, a notification that an insulin injection is required, or a notification that emergency medical assistance is required. In some embodiments, the injection device 256 may vibrate to alert a user to a notification. In some embodiments, the injection device 256 may produce an auditory transmission, such as a chirp, beep, or ringtone, to alert a user to a notification. Notifications may also be transmitted to external devices, such as the smart phone 252, and to medical personnel for data tracking or emergency services.

Figure 2A:
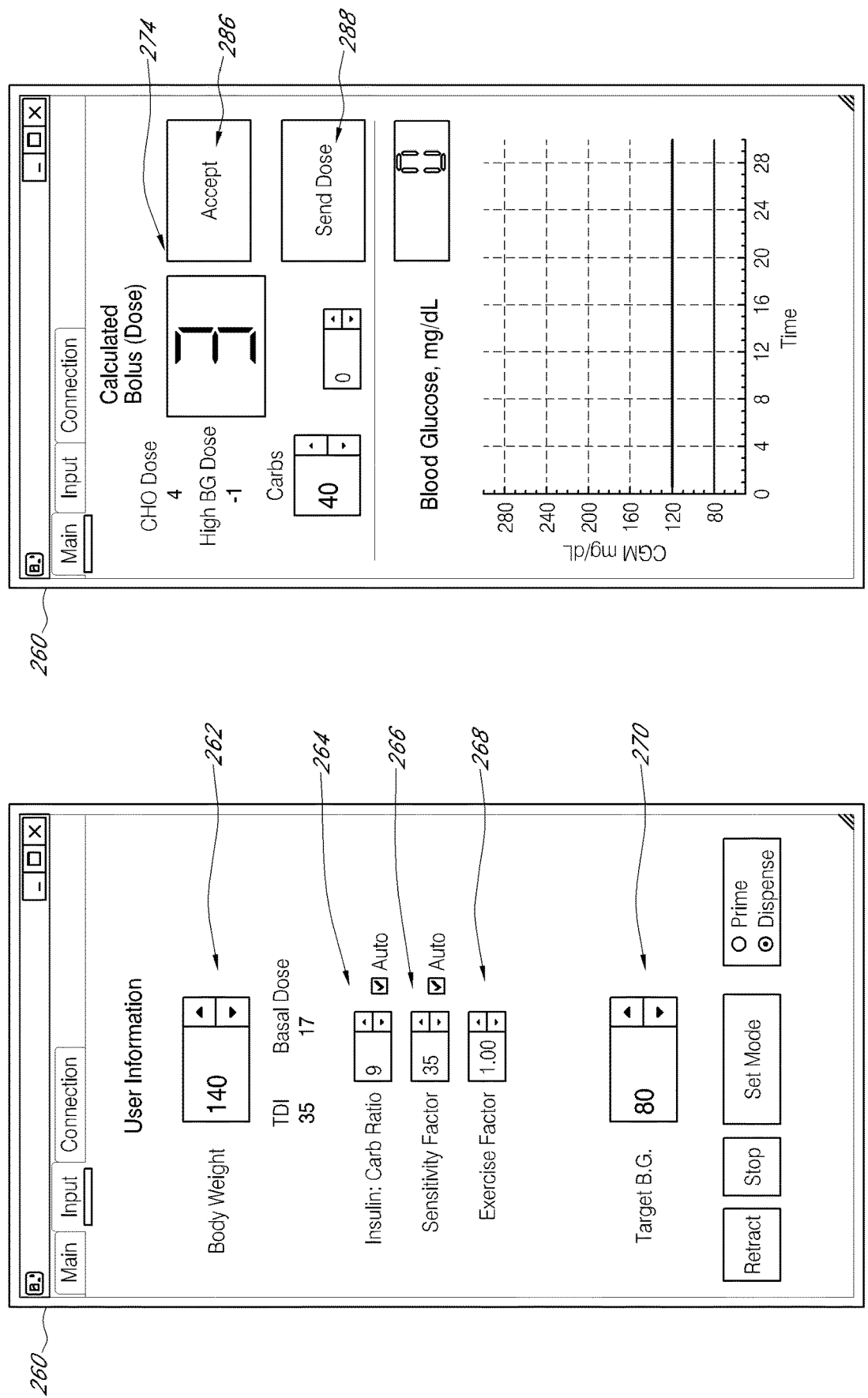
FIGS. 2A and 2B illustrate screenshots of an exemplary embodiment of the invention.

FIG. 2A illustrates an exemplary screenshot 260 of a smart phone application running on a smart phone, such as smartphone 252, in accordance with an exemplary embodiment of the invention. Screenshot 260 depicts user inputs for body weight 262, insulin-to-carbohydrate ratio 264, sensitivity factor 266, exercise factor 268, and target blood glucose 270. The inputs can be entered using a user interface on the smart phone 252. In some embodiments, one or more of the inputs may be received from an external device. For example, body weight 262 may be received from a scale or weight monitoring application. The exercise factor 268 may be based on exercise data received from an activity monitoring device or application. The insulin-to-carbohydrate ratio may be based on data received from a diet monitoring device or application. The sensitivity factor may be based on data received from one or more of a continuous glucose monitor, a blood glucose monitor, and a smart injection device. The smart phone application may also receive data from a sleep monitoring device or application. The smart phone may also receive data related to other medicine used by the patient. The smart phone application preferably determines the total daily insulin and basal dose 274 based on the patient's weight. A bolus dose is estimated using the insulin-to-carbohydrate ratio 264, the sensitivity factor 266, and the exercise factor 268. In one exemplary process, the following determinations are made. First, total daily insulin (TDI), in units, is determined as body weight in pounds divided by four (4). A basal dose is set at 40-50% of the TDI. Overnight insulin preferably remains constant. A bolus dose is set at 50-60% of the TDI, taking insulin-to-carbohydrate ratio 264, sensitivity factor 266 and exercise factor 268 into account. The application assumes that one unit of rapid acting insulin will metabolize 12-15 grams of carbohydrates. The application also assumes that one unit of rapid acting insulin is required to lower blood glucose by 50 mg/dl.

Once the dose is determined, the injection device 256 may inject the determined dose. As discussed below with reference to FIG. 3A, the user can prime the insulin cartridge by selecting the "prime" screen from the user interface of the injection device 256. Pressing the enter button 302 and then selecting the prime function followed by pressing the inject/prime button 301 causes the injection device 256 to extend a plunger into a medicament cartridge, causing the medicament cartridge to expel fluid from a needle. The plunger may be stopped manually when the prime button 301 is released (such as when the patient observes fluid exiting the needle). In another embodiment, the auto-prime function can be used in which a fixed volume of fluid, e.g., 3 units (or 30 microliters), is expelled.

Figure 2B:
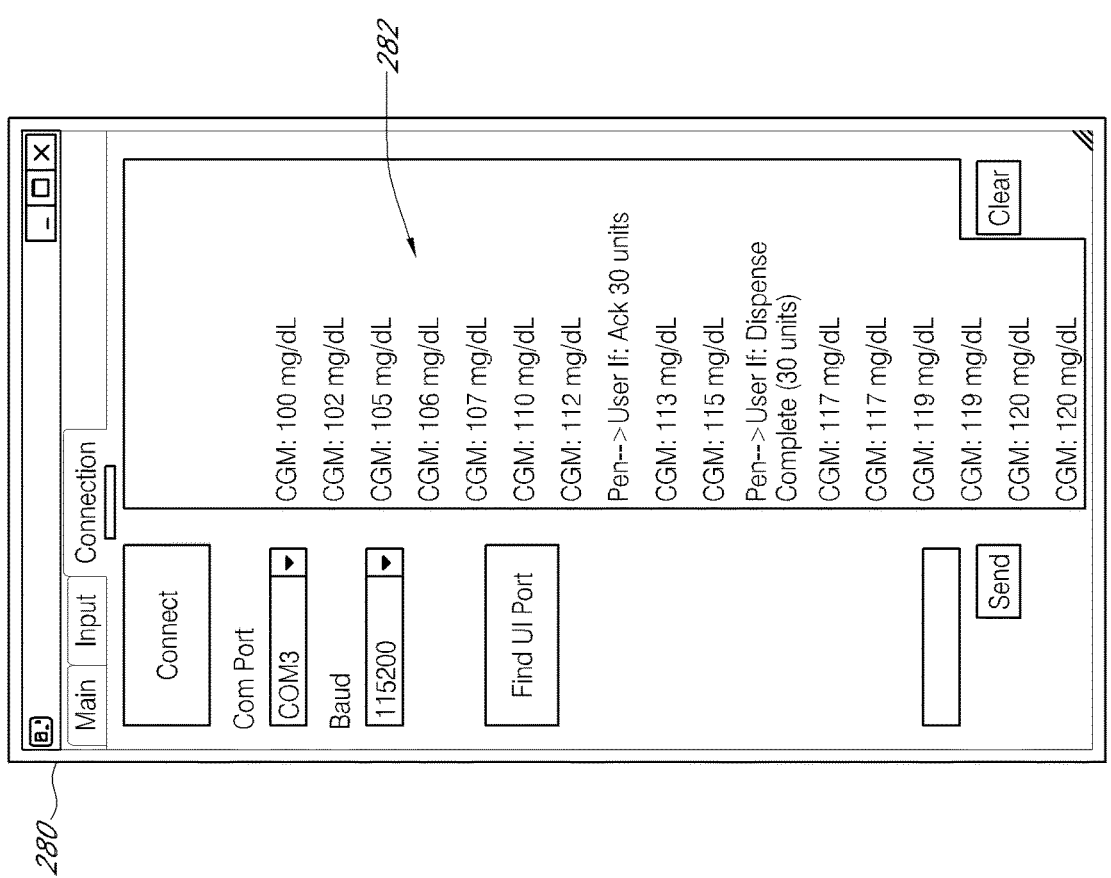

FIG. 2B illustrates another exemplary screenshot 280 of a smart phone application running on a smart phone in accordance with an exemplary embodiment of the invention. Screenshot 280 illustrates a blood glucose history 282 generated from data received from the CGM 254. CGM data is preferably transmitted from the CGM 254 to the smart phone application every 10 seconds. In some embodiments, the CGM 254 is in continuous, near continuous, or regular communication with the smart phone application. Target high and low blood glucose levels are preferably highlighted in the blood glucose history 282. The appropriate bolus dosage is determined based on prior user information including body weight, target glucose, insulin-to-carbohydrate ratio, and the most recent blood glucose value received from CGM 254. The determined dose is displayed in the determined dose field 284 of the user interface. To initiate a dose as determined, the user selects the "accept" button 286 on the smart phone user interface. The user interface also preferably includes "up" and "down" arrow buttons to adjust the dose as needed. The "send dose" button 288 causes the smart phone application to transmit the dose information to the injection device 256. The injection device 256 includes an "inject" button that, when pressed, initiates injection of the determined and transmitted dose.

Figure 2C:
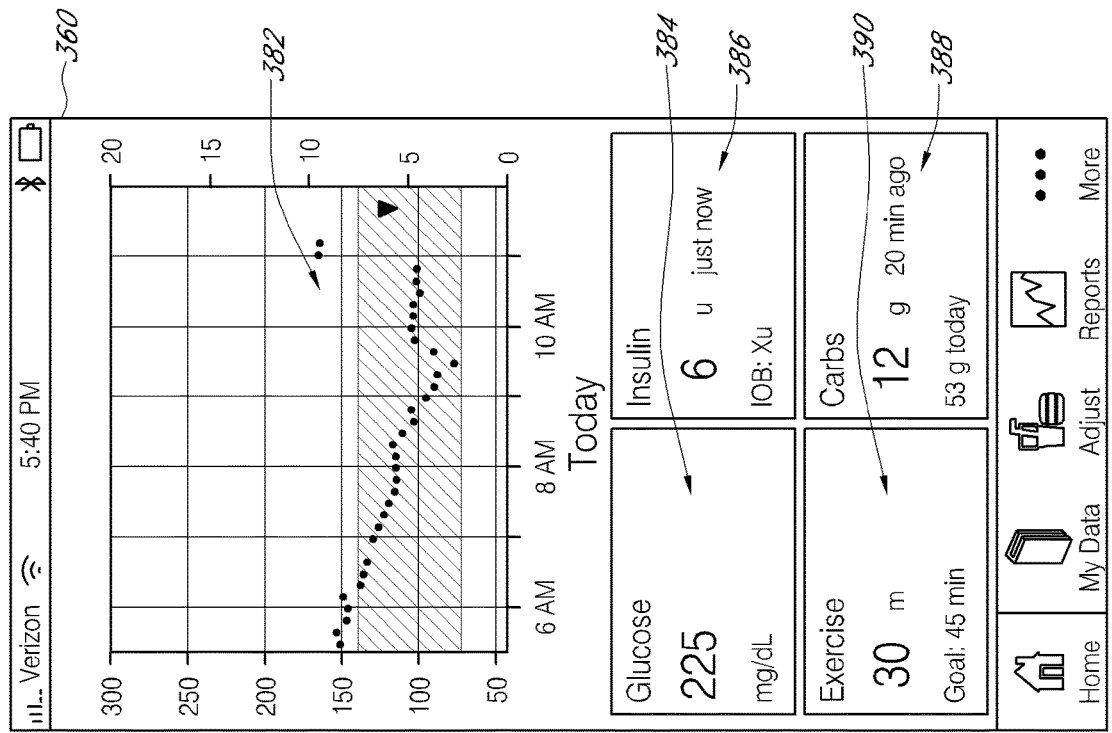
FIG. 2C illustrates additional screenshots of an exemplary embodiment of the invention.

FIG. 2C illustrates exemplary screenshots of a smart pen application running on a smart phone in accordance with an exemplary embodiment of the invention. Screenshot 360 illustrates a blood glucose history 382 generated from data received from the CGM 254. CGM data is preferably transmitted from the CGM 254 to the smart phone application as specified above. A plot of blood glucose history 382 generated from data received from the CGM 254 shows blood glucose level trends. To help the patient further, other clinically relevant information such as a most recent blood glucose data 384 that was transmitted from CGM 254 and used for dose determination and also a most recent insulin dose injection 386 are shown. Data for the most recent insulin dose injection 386 can be received from the injection device 256. In some embodiments, the injection device 256 is in continuous, near continuous, or regular communication with the smart phone application. Exercise goal and current progress data is displayed in field 390. Exercise data may be received from a physical activity monitoring device or application. Other relevant information such as Carbs consumption for the day is displayed in field 388. Carbs consumption can be based on diet information received from a diet monitoring device or application.

Screenshot 361 illustrates an adjustment screen. A current glucose 362 is shown. A target blood glucose 364 is also shown, and preferably highlighted in the glucose history 382 of screen 360. A determined bolus dosage 366 is determined based on prior user information including target glucose and the most recent blood glucose value received from CGM 254. The determined dose is displayed in the determined dose field 366 of the user interface. To finalize the injection, the user interface is preferably used to adjust the dose based on the Carbs 368 as needed. The final determined dose 370 is used by the injection device 256 to perform the injection. The injection device 256 includes a button or trigger that, when engaged, initiates injection of the determined dose.

In an alternative embodiment, the smart phone application features described in reference to FIGS. 2A-C may instead be integrated into the user interface of the injection device 256. Data may be received, continuously, near continuously, regularly, or intermittently, from one or more external devices or via a user interface of the injection device 256.

Figure 3:
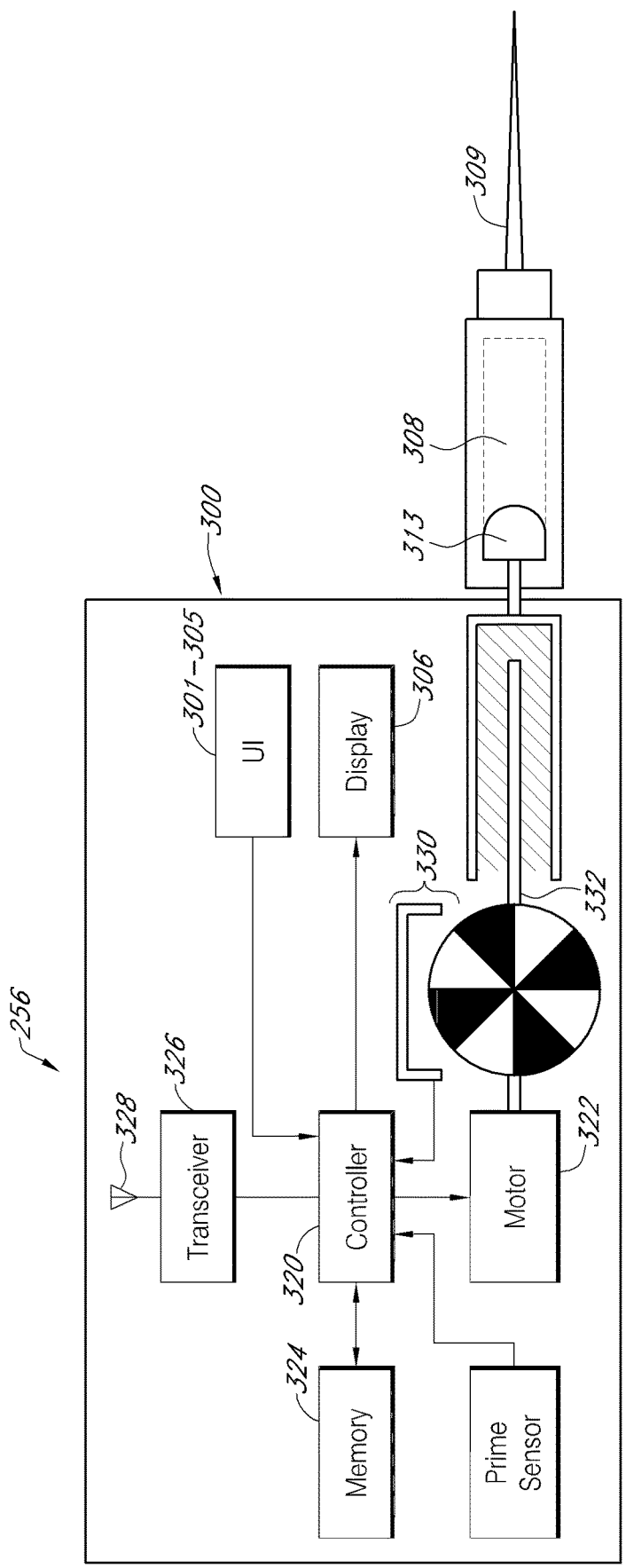
FIG. 3 is a block diagram of a smart bolus injector according to an exemplary embodiment of the invention.

FIG. 3 is a block diagram of the smart pen injection device 256 described above. The injection device 256 includes a controller 320 for controlling a motor 322 and a display 306. The injection device 256 further includes a memory 324 for storing program instructions as well as data. The injection device 256 is configured to continuously, or near continuously, communicate with one or more external devices, such as for example, a continuous glucose monitor, a computing device, an exercise monitoring device, a sleep monitoring device, a diet monitoring device, and a scale. The injection device 256 preferably includes a wireless transceiver 326 and internal antenna 328 for communicating with other devices wirelessly. The injection device 256 can also include a wired communication interface.

The injection device 256 further includes a motor 322, a shaft 332, a plunger 313, an insulin cartridge 308, and a pen needle 309. In response to receiving instructions to perform an injection, the controller 320 activates the motor 322. The motor 322 is engaged to the shaft 332. When activated, the motor 322 can cause the displacement of the shaft 332. The shaft 332 is engaged to the plunger 313. The insulin cartridge 308 is sealed at a proximal end of the cartridge by the plunger 313, which is adapted to slide within the cartridge 308 and change the volume of the cartridge 308 in response to displacement of the shaft 322. The pen needle 309 is engaged to the distal end of the cartridge to dispense medicament as the volume of the cartridge is reduced by plunger movement of plunger 313. In some embodiments, controller is configured to set a medicament delivery amount by setting a displacement distance of the movable plunger 313. An encoder 330 is preferably connected to the shaft 332 of the motor 322, and provides encoder signals corresponding to motor movement to the controller 320. The encoder 330 can include a sensor adapted to sense movement of the encoder 330 and to provide signals indicative of encoder movement to the controller 320. Accordingly, the encoder signals received by the controller 320 from the encoder 332 are indicative of movement of a plunger 313 within a medicament cartridge 308. The controller 320 can be configured to control the medicament delivery amount based on the signals received from the encoder 330. In some embodiments, the motor 322 is adapted to displace the plunger for the duration of a control signal.

Figure 3A:
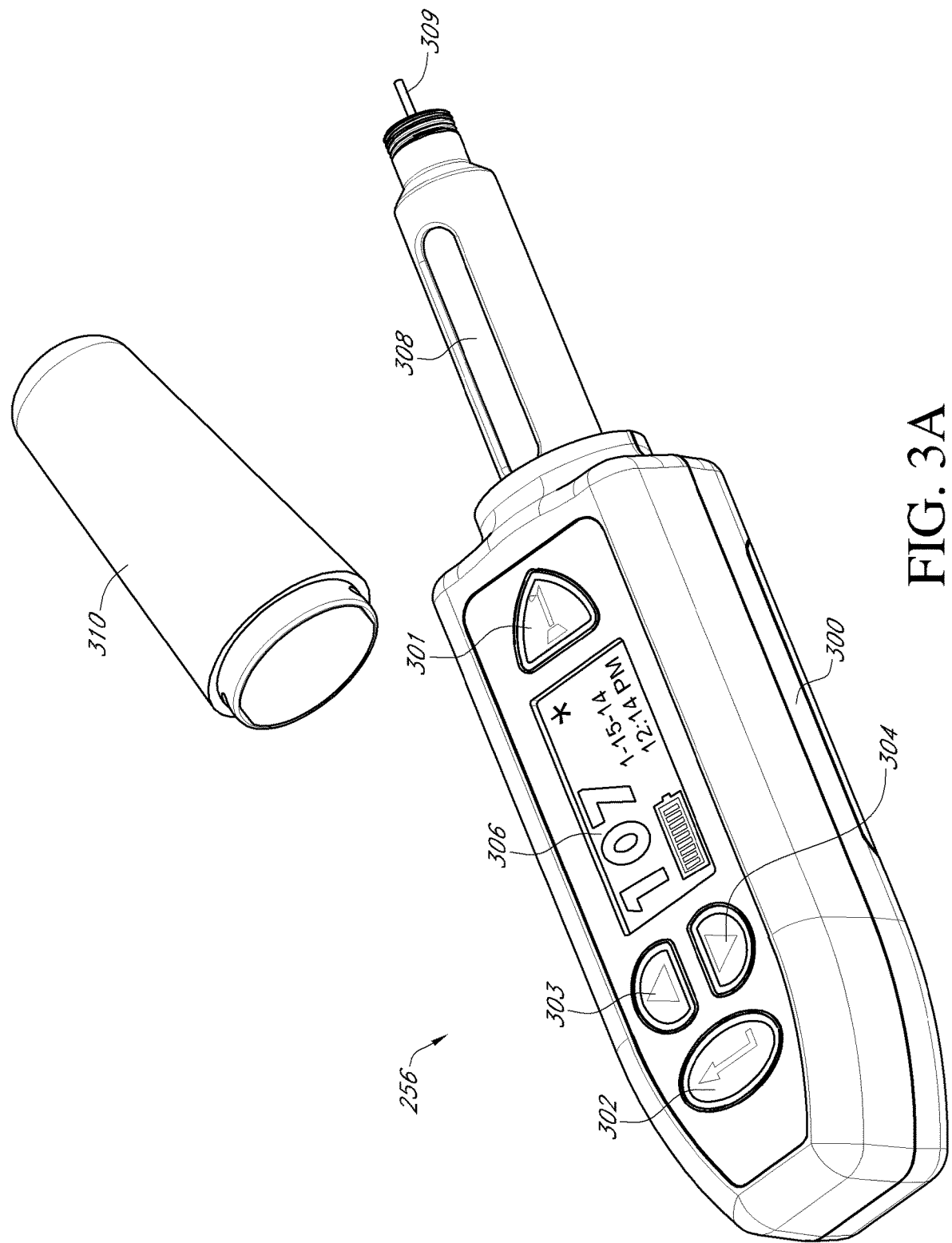
FIG. 3A is an isometric view of the smart bolus injector of FIG. 3.

FIGS. 3A-3D illustrate an exemplary embodiment of a smart pen injection device 256. FIG. 3A depicts a perspective view of the injection device 256. The injection device 256 includes a main housing 300, user interface buttons 301-304, a display 306, an insulin cartridge 308, a pen needle 309 and a cap 310. The user interface buttons 301-304 and the display 306 are positioned on the surface of the main housing 300. The insulin cartridge 308 protrudes out from and is engaged to one end of the main housing 300. The pen needle 309 protrudes out from and is engaged to the end of the insulin cartridge 308 opposite the main housing 300. The cap 310 is configured to fit over the insulin cartridge 308 and the pen needle 309. The cap 310 is further to engage with and removable secure to the main housing 300. The user interface button 301 can be configured to cause an injection upon engagement. The user interface buttons 303 and 304 can be configured to select between one or more options displayed on the display 306. The user interface button 302 can be configured to cause the display 306 to revert to a previous configuration.

Figure 3B:
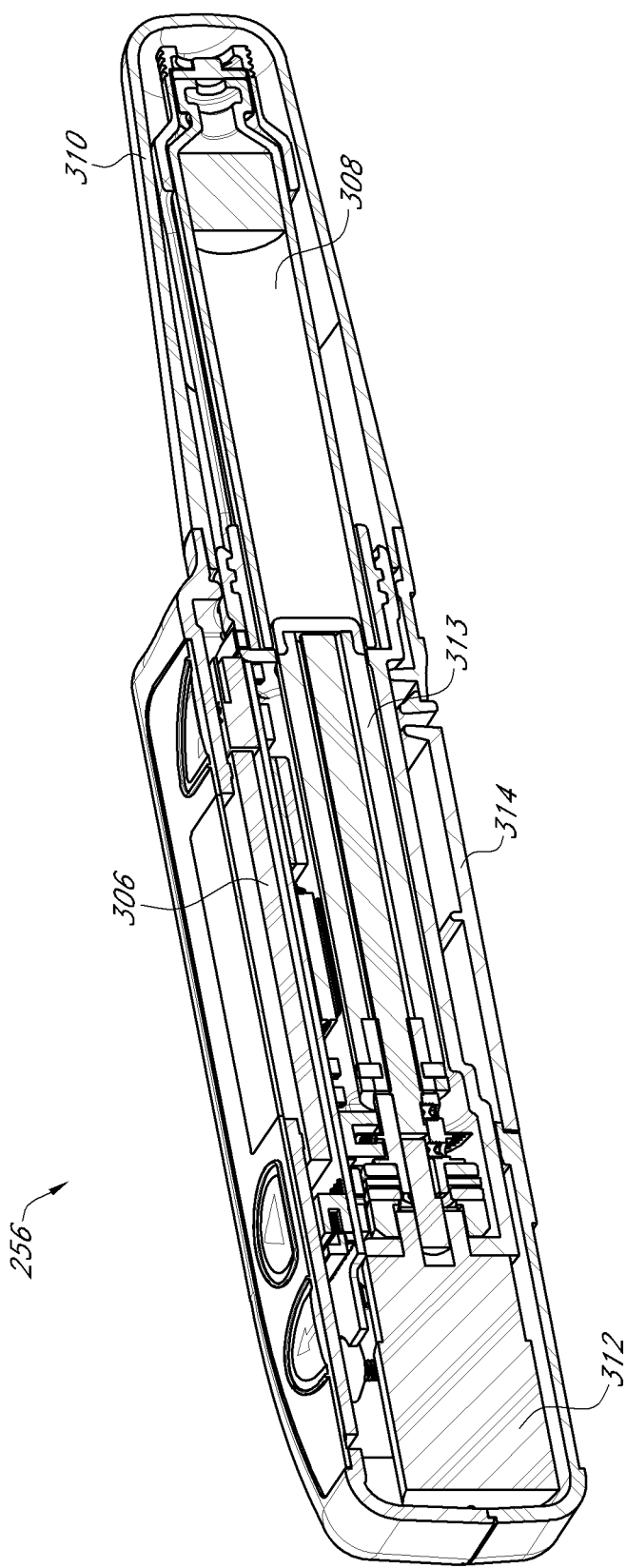
FIG. 3B is a section view of the smart bolus injector of FIG. 3.

FIG. 3B shows a cross sectional view of the injection device 256. Inside the housing 300 resides electronics, including the motor 312, the plunger 313, and a gear 314. In some embodiments, the motor 322 can cause movement of the gear 314. In response, the gear 314 can cause the displacement of the plunger 313 along a primary axis of the insulin cartridge 308.

Figure 3C:
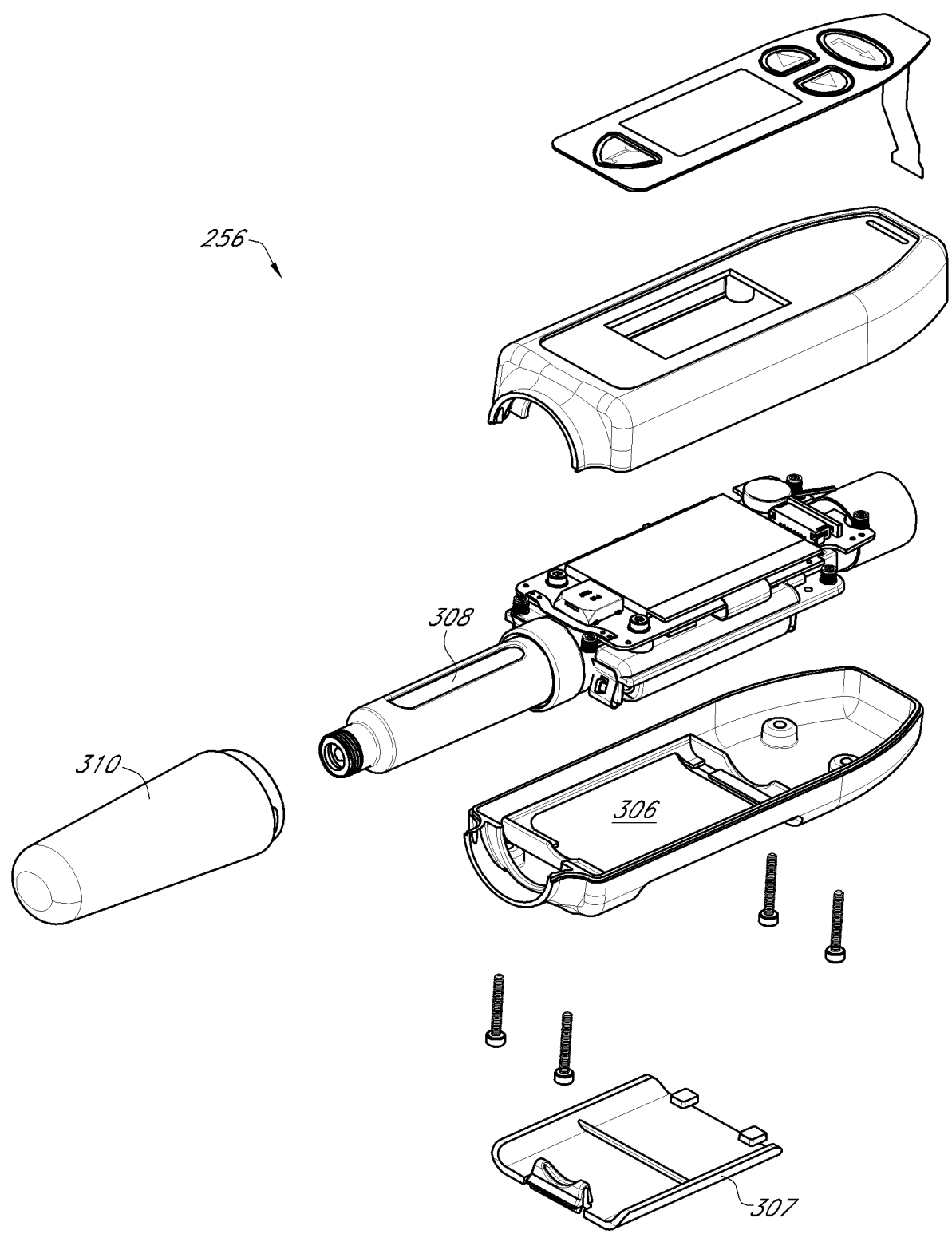
FIG. 3C is a top exploded view of the smart bolus injector of FIG. 3.
Figure 3D:
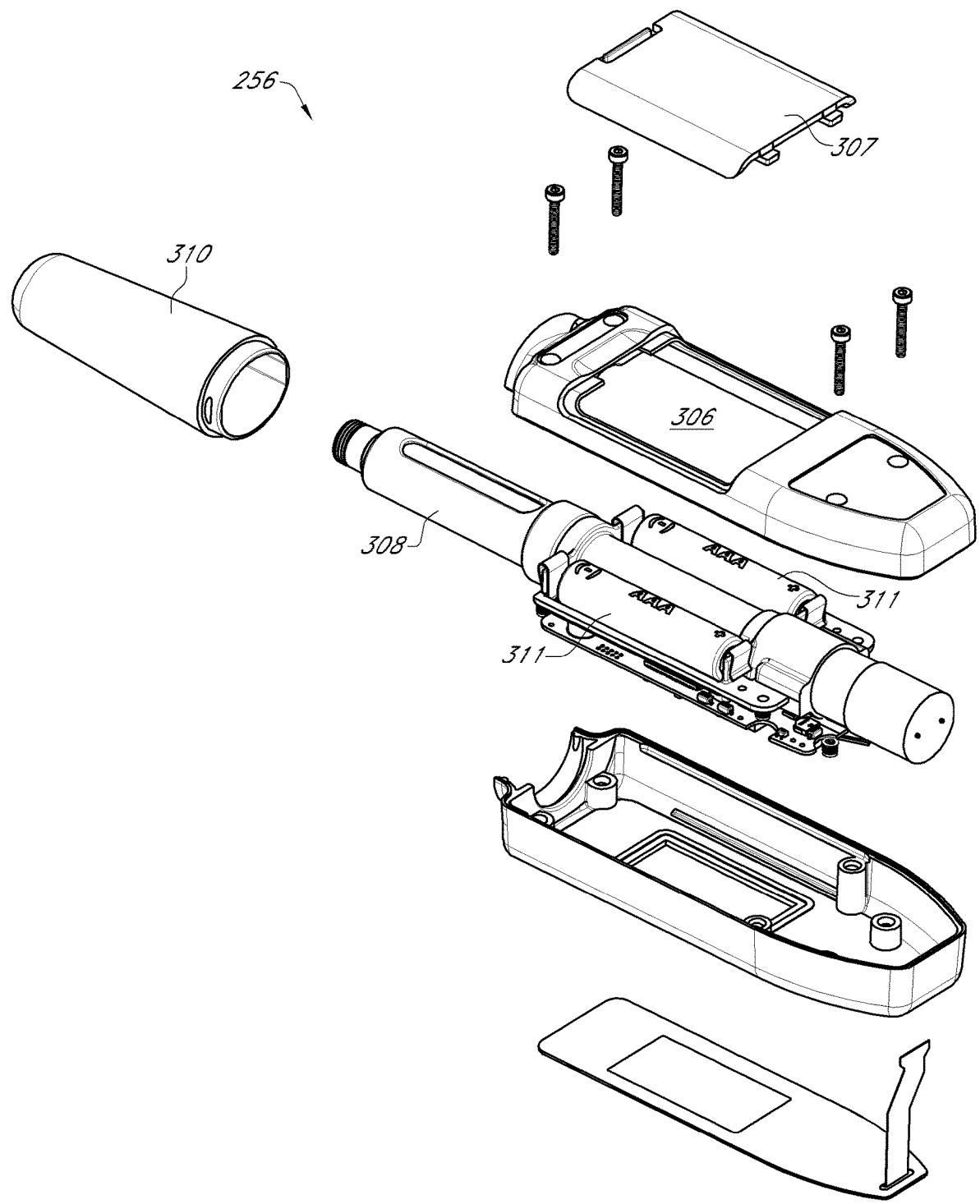
FIG. 3D is a bottom exploded view of the smart bolus injector of FIG. 3.
Figure 3E:
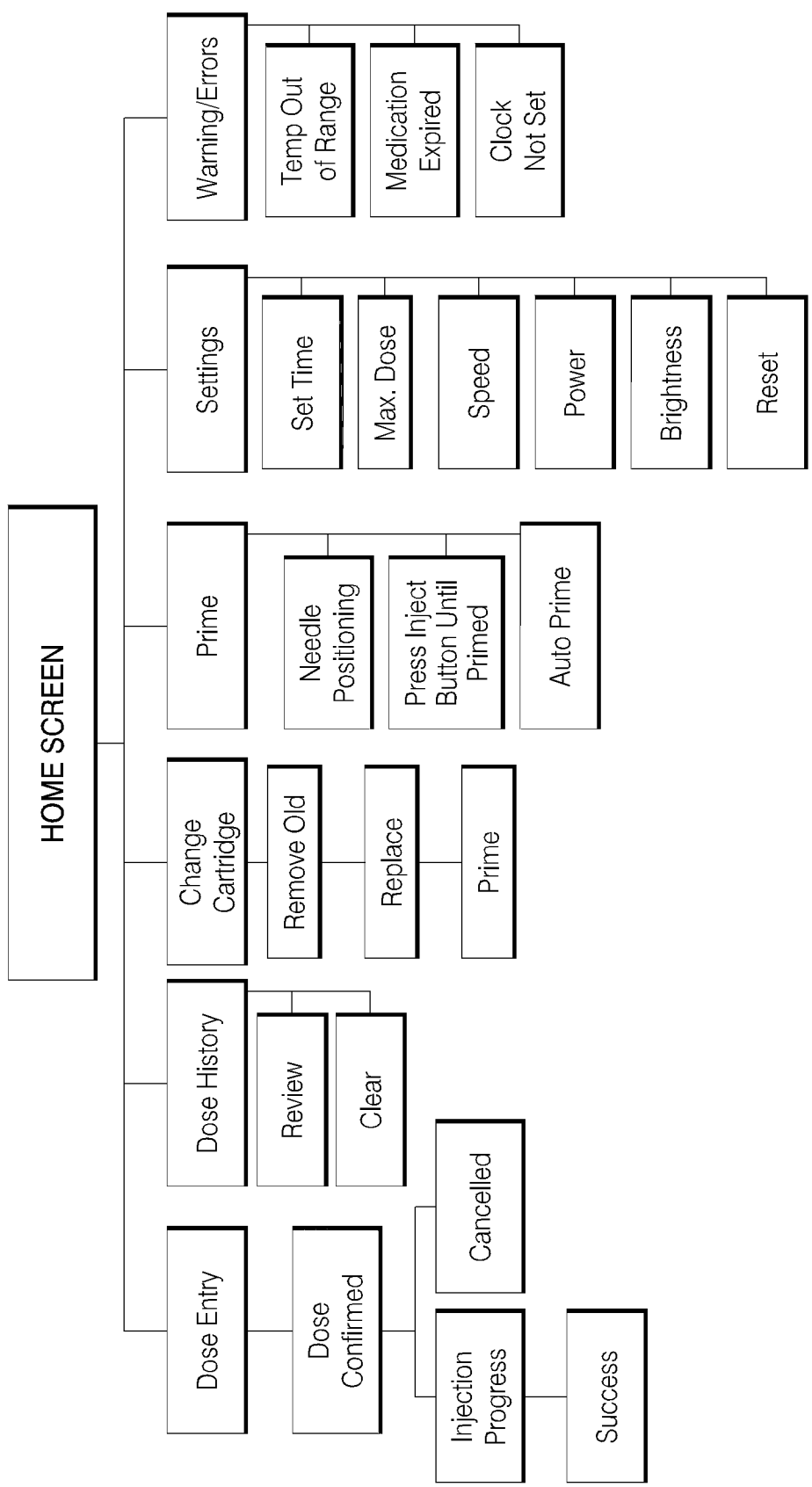
FIG. 3E is the flow diagram of user interface screens of the smart bolus injector of FIG. 3 with each box representing a separate screen on the device.

FIGS. 3C and 3D depict a top exploded view and a bottom exploded view, respectively, of the injection device 256. Inside the housing 300 further reside one or more batteries 311. The housing 300 further includes a battery compartment cap 307 which is removably secured to the housing 300. The battery compartment cap 307 can be removed from the housing 300 to allow for access to the batteries 311.

A preferred embodiment of the invention is battery powered, preferably at 3 VDC. The device is preferably equipped with a 12 mm gear motor, at a 100:1 gear ratio to drive a 2-56 threads per inch lead screw to generate injection force against a pusher bar with anti-rotation to push a plunger against the cartridge stopper. The gear motor design incorporates a rotary optical encoder with a photo-interrupter sensor to accurately control the plunger speed. The system also provides a highly accurate position sensing, index/end-of-travel and safety interlock. The specified motor drive system preferably generates about 30 psi pressure with standard 29, 30 and 31 gauge needles at approximately 3 pound force load, and up to 160 psi under occlusion. The 30 psi exceeds the pressure requirements for subcutaneous injection. The 160 psi meets the pressure requirements for intradermal injection. The delivery accuracy of the system using a 3 ml insulin cartridge (with no load) is equivalent to delivering 30 units of insulin in 5 seconds.

FIG. 3E illustrates an exemplary user interface flow diagram, wherein each box represents screens presented on the device. The user interface can include a "home screen", from which one or more other display screens can be selected. The user interface can also include a "dose entry" screen which allows for the receipt, entry, and display of dose information. The dose entry screen may also include a "dose confirmation" field. The dose confirmation field may include an "injection progress" field, a "success" status field, and a "cancelled" status field. The user interface may further include a "dose history" screen, which can include information related to previous injection events. The dose history screen can include a "review" field and a "clear history" field, allowing for the deletion of information regarding previous injection events. The user interface may further include a "change cartridge" screen, which includes information related to the status of the insulin cartridge 308 within the injection device 256. The change cartridge screen may include a "remove old" field which can indicate that the insulin cartridge 308 is in a condition for removal from the injection device 256, a "replace" field which can indicate that the insulin cartridge 308 is in a condition for replacement, and a "prime" field which can indicate that the insulin cartridge 308 is in a condition for priming. The user interface may also include a "prime" screen, which allows for entry and display of priming information. The prime screen may include a "needle positioning" field which can include information related to the position of the needle 309, a "press inject button until primed" field which can allow for the selection of a priming option in which the user presses the inject button until the injection device 256 is primed, and an "auto prime" field which can allow for the selection of a priming option in which the injection device 256 is automatically primed. The user interface further includes a "settings" screen, which can allow for the selection of a plurality of settings related to the injection device 256. The settings screen includes a "time set" field which can allow for the selection of a time, a "maximum dose" field which can allow for the selection of a maximum dose, a "speed" field which can allow for the selection of the speed of the injection device 256, a "power" field which can allow for the selection of the power of the device 256, a "brightness" field which can allow for the selection of the brightness of the display 306, and a "reset" field which can allow for the resetting of one or more settings to original conditions. The user interface further includes a "warning/errors" screen that can display warning messages to a user. The warning/errors screen includes a "temperature out of range" field which indicates that the temperature of the insulin is outside of a predefined range, a "medication expired" field which indicates that the insulin has expired, and a "clock not set" field which indicates that a time setting has not been selected.

Figure 4:
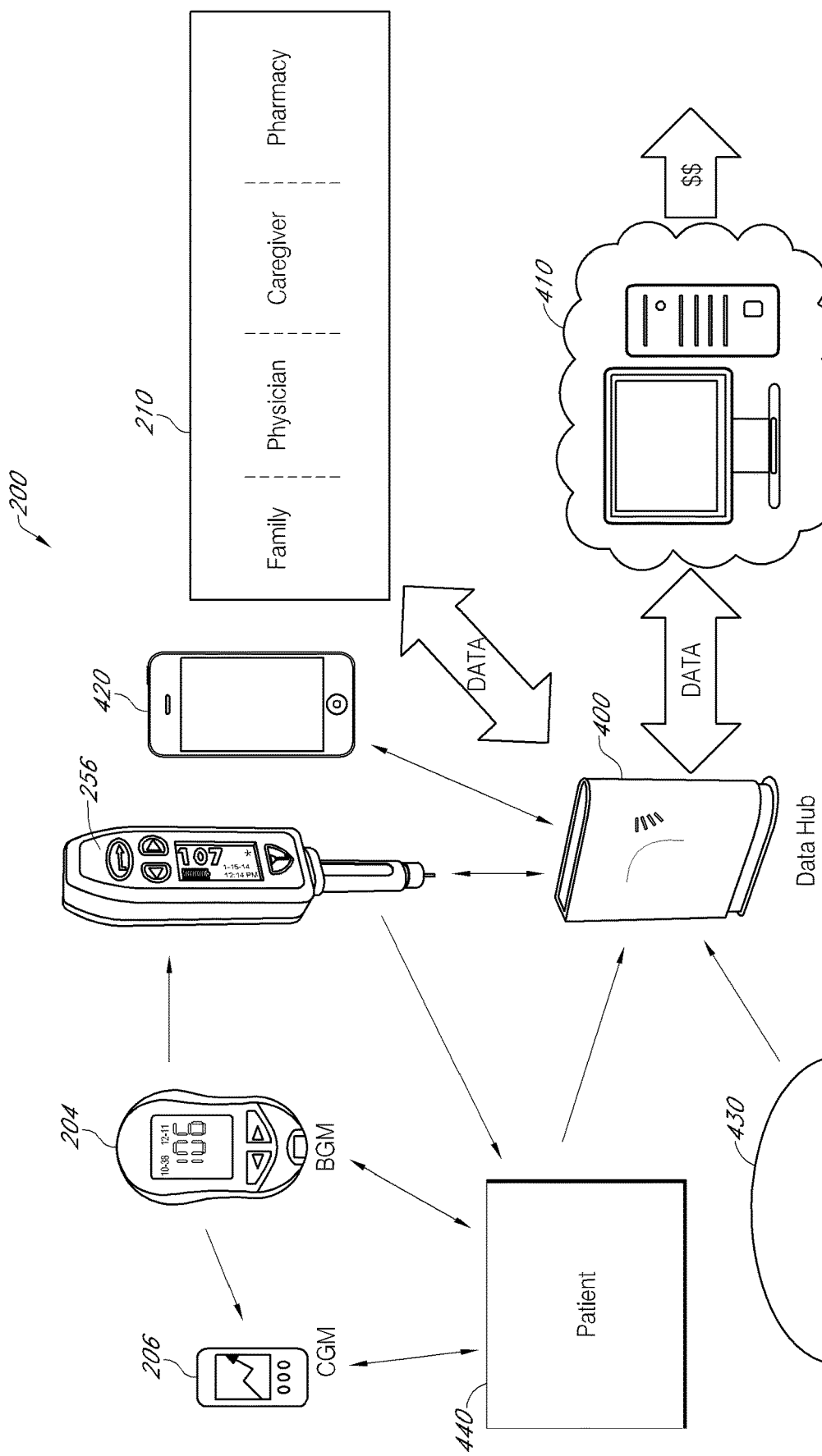
FIG. 4 illustrates a system including a health management access point according to another exemplary embodiment of the invention.

FIG. 4 illustrates a system according to an embodiment of the present invention for medication adherence and wellness monitoring. A central feature of this embodiment is a data hub 400 that wirelessly communicates with other components in the system, including a smart injection device 256, a health management access point 210, a remote server 410, a smart phone 420, and receives optional wellness data from partner companies via component 430. Server 410 is preferably used as access to data by insurance companies or other similar third party entities with authorized access to the data. A BGM 204 or a CGM 206 are preferably wirelessly connected to smart injection device 256 to provide glucose readings to the injection device 256. In some embodiments, the BGM 204 or the CGM 206 are in continuous, near continuous, or regular communication with the injection device 256. Glucose readings, and other data as will be discussed further below, are used to determine a medicament dose for the patient 440. Smart injection device 256 sets the dose amount based on the determined medicament dose. The smart injection device 256 self primes the medicament cartridge prior to injection, informs the patient 440 that the dose is ready for injection, and then dispenses the dose when the patient injects the pen needle and presses a "dispense" button on the smart injection device 256. The results of the injection, including dose amount, time of injection, and whether the injection was successful, are stored in a memory of the injection device 256 and transmitted to the hub 400. The smart injection device 256 may be in continuous, near continuous, or regular communication with the hub 400. The injection device 256 may communicate with one or more devices through suitable communication technology including a cellular network, a wireless network, such as Wifi, Bluetooth, and Zigbee, or a wired network. From the data hub 400, historical data including glucose readings and injection data may be transmitted to health management access point 210 and/or remote server 410.

The hub 400 may also receive data from the smartphone 420, which can include inputs and instructions from a user. The component 430 can include one or more devices for monitoring wellness data, which can include data related to exercise, diet, sleep, weight, and other medicines used by the patient. The wellness data can be transmitted to the hub 400 where it can be used for determining a medicament dose at the hub 400 or transmitted to the injection device 256 for determination of a medicament dose.

Some injection related data may be transmitted from the hub 400 to the health management access point 210, from which the data can be accessed by one or more third parties, such as for example, a family member of the patient, a physician, a caregiver, or a pharmacy. The health management access point 210 may further allow for the input of data by one or more of the physician, caregiver, or pharmacy, which can be transmitted to the hub 400 and used in determining a medicament dose.

In one embodiment, an exemplary smart bolus injector enhances the attributes of BD's Glucose Binding Protein-Based Continuous Glucose Monitoring (GBP CGM) by integrating the bolus injector with a GBP CGM, the delivery system advantageously provides a less invasive alternative as compared to a conventional insulin infusion pump combined with a Glucose Oxidase based CGM or a conventional smart pen used together with episodic capillary blood glucose self-monitoring (BGM). Glucose Binding Protein and continuous glucose monitoring is described in Continuous Glucose Monitoring Using a Novel Glucose/Galactose Binding Protein: Results of a 12-Hour Feasibility Study with the Becton Dickinson Glucose/Galactose Binding Protein Sensor; Kevin Judge, M.D., Linda Morrow, M.D., Alexander G. Lastovich, M.Eng., David Kurisko, M.B.A., Steven C. Keith, M.S., Jacob Hartsell, M.S., Bruce Roberts, Elaine McVey, MStat, Kristin Weidemaier, Ph.D., Khin Win, M.D., and Marcus Hompesch, M.D., as well as U.S. Pat. No. 6,855,556, issued Feb. 15, 2005, U.S. Pat. No. 7,851,593, issued Dec. 14, 2010, U.S. Pat. No. 7,496,392, issued Feb. 24, 2009, U.S. Pat. No. 7,787,923, issued Aug. 31, 2010, U.S. Pat. No. 7,792,561, issued Sep. 7, 2010, and U.S. Pat. No. 8,623,639, issued Jan. 7, 2014, the entire contents of each of which are hereby incorporated by reference.

One embodiment provides the means to improve upon the performance of standard pen or syringe injector devices by taking advantage of CGM attributes. CGM advantageously helps patients become more aware of their glucose levels and how they can change based on food, exercise, medication, or other activities. Using a CGM monitor together with an exemplary bolus injector system as described herein allows patients to feel more confident about the way they are managing their diabetes, and can subsequently improve outcomes and help lower their HbA1c (glycated hemoglobin) levels.

One advantage of an exemplary smart bolus injector integrated with a CGM is to help diabetic patients achieve their therapeutic goal to lower their HbA1c level. To prevent extreme glucose fluctuations, most insulin users check their blood sugar 2-6 times per day, depending on their therapy regimen. For standard Pen/BGM users, this will require use of two separate devices with multiple steps and multiple needle sticks for each. Exemplary embodiments of the invention preferably and advantageously combine the functions of an insulin pen, pen needle, and CGM monitoring into a single less invasive device that obtains the patient's glucose reading as well as delivering their insulin with fewer needle sticks. This provides a more convenient solution and encourages greater glucose testing frequency and provides patients and their healthcare providers with the blood glucose data to make better dosing decisions.

It should be understood that the smart bolus injector described above may be used within an artificial pancreas system. The bolus calculator need not be separate, but may be tied into a continuous glucose processing control system. The benefit for such a system is that the bolus can be better determined within the context of continuing basal determinations to improve medication outcomes and quality of care.

An exemplary embodiment of the invention includes a safety feature to shutoff the delivery system when hypoglycemia (low blood sugar) is detected. This feature responds to low blood glucose readings from the glucose sensor by stopping the bolus injector from delivering insulin. For patients who are experiencing low blood glucose, the system will also preferably provide personalized instructions on how to obtain and receive a glucagon (GLP-1) injection or any other personalized measure.

An exemplary embodiment of the invention may be used by people who are using an insulin pump with CGM but who want to use a less restrictive and simpler insulin delivery system such as a bolus injector wirelessly connected to a CGM, either permanently or on a temporary basis.

Another advantage of an exemplary embodiment of the invention is that the smart bolus injector may be also used together with an insulin infusion pump to prolong the life of the pump reservoir, or to allow the use of a pump with less driving power or less pressure. The smart bolus injector can be configured to wirelessly communicate with the insulin infusion pump. In some embodiments, the smart bolus injector and insulin infusion pump are in continuous, near continuous, or regular communication.

Preferably, embodiments of the invention have a manual feature that permit the smart bolus injector to function like a conventional pen needle in case of an emergency or other malfunction of other components of the overall system.

Another advantage of exemplary embodiments of the present invention is high pressure delivery of medicament. The exemplary bolus injector system improves upon the performance of standard pen and syringe injector devices and/or insulin pumps, or any other similar devices with a primary reservoir or cartridge, by providing the specific needle delivery forces required to facilitate user/patient delivery of medicaments with high viscosity or of medicaments with standard viscosity into the dense intradermal space where the force requirement may be higher.

A preferred embodiment of the present invention preferably provides tactile and visual feedback to the user. The visual feedback may be monitored on the injector display screen. However, other embodiments may only provide one of tactile or visual feedback, or other types of feedback alone or combined, such as auditory feedback. Other embodiments may not provide feedback to the user.

Wearing a pump can be inconvenient for patients. This is particularly true for active patients, for patients at the beach or asleep. Generally it is inconvenient for users to be connected to a conventional insulin pump. By switching to an exemplary bolus injector system according to an embodiment of the invention a patient can disconnect from the pump for short periods or even permanently.

Embodiments of the present invention also minimize the risk of infection associated with conventional insulin pump systems. If patients fail to change the insertion site of the cannula of a conventional insulin pump every two or three days the risk of infection increases. Embodiments of the present invention more closely resemble simpler injection systems with the accompanying reduced risk of infection associated with a cannula that remains in the patient's skin for several days.

Embodiments of the present invention provide a near closed loop injection system that controls the volume of liquid medicament introduced into the body of a user. For a conventional insulin infusion pump, the infusion rate of the fluid is controlled. A closed loop system includes a sensor system such as a CGM and a delivery system. In embodiments of the invention the sensor signal is used to generate a controller input to operate the delivery system. Embodiments of the present invention preferably deliver liquid into the user at fixed volumes, rather than a rate. The volume is set by commands from a controller. In a diabetes application, the sensor system monitors the glucose concentration in the body of the user, and the liquid introduced by the delivery system into the body of the user includes insulin. The sensor system uses the sensor signal to generate a message that is sent to the delivery system. The message includes the information used to generate the controller input. The sensor may be a subcutaneous sensor such as a GBP CGM in contact with interstitial fluid. Controlling the fluid delivery by bolus volume, as compared to infusion rate, significantly shortens the time scale for delivery and is more convenient for the patient.

Embodiments of the present invention advantageously perform insulin pump functions with high accuracy but without the burden of being directly attached to the patient's body like a conventional insulin pump. For simplicity and convenience, the system is preferably designed to include automation and form factors in order to reduce the hassle of reservoir change and priming to make it more intuitive and user friendly. Furthermore, for ease of use and ease of commercialization, a bolus auto injection system according to an embodiment of the invention may be constructed using standard pen injector parts such as commercially available prefilled insulin cartridges and pen needles. For example, the device may employ a 300 unit insulin supply and a 5 mm long 31 G BD pen needle. The system is preferably reusable to keep the cost per injection to a minimum, and to increase the likelihood of patient adoption and affordability. Furthermore, as component costs for the system come down, a smart bolus system could be embodied in prefilled disposable pens.

Embodiments of the present invention continuously monitor glucose levels either by communicating with a separate CGM component, or by incorporating a blood glucose monitoring component. The device preferably prepares the device with the required insulin dose for a pre-scheduled and/or an on-demand insulin injection. It should be understood that the device may be integrated with any glucose monitoring system including a GBP CGM, a Glucose Oxidase based CGM, or an episodic capillary blood glucose self-monitoring (BGM).

Figure 5:
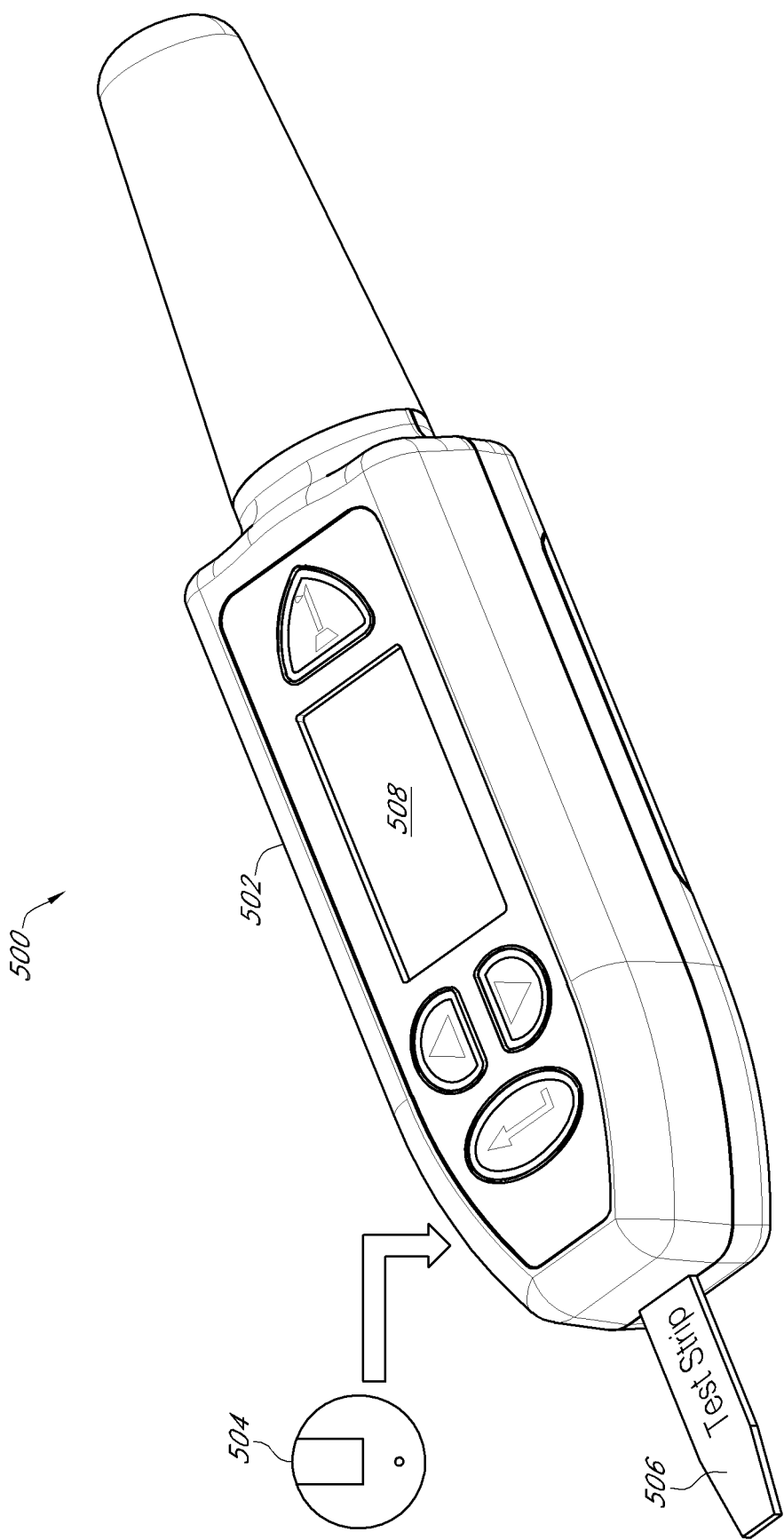
FIG. 5 illustrates an integrated smart pen and BGM device according to an exemplary embodiment of the invention.

Another exemplary embodiment of a system according to the invention is described in connection with FIG. 5. This system 500 preferably includes an insulin Smart Pen 502, an integrated (embedded) BGM sensor 504, a BGM Test Strip 506, and a display 508. In a single device format, a miniaturized digital low cost BGM sensor 504 is incorporated into the pen hardware. The BGM sensor 504 measures a patient's blood glucose from the test strip 506 and then preferably displays the measured blood glucose results on the smart pen display 508. A preferred embodiment of the invention measures a patient's blood glucose first and then determines an insulin dose and delivers the needed insulin in a single integrated device.

A preferred embodiment of the invention is to perform blood glucose measuring, insulin injection in connection with a patient maintaining journal records all in the same device. This embodiment advantageously combines the features of several devices into one single device and, thereby for simplicity and convenience, replaces multiple devices into one self-care device.

An exemplary system 600 that is bolus injector centric will now be described in connection with FIG. 6. This embodiment relies significantly on a handheld model of a smart bolus device. The smart bolus device 602 preferably includes a large display screen 604 such as an OLED screen to provide injection information. The smart bolus device 602 also includes communication components to perform data transfer. Data transfer is preferably to or from the cloud, and may be accomplished by any suitable means including a cellular network, a wireless network, such as Wifi, Bluetooth, Zigbee, or a wired network. In this embodiment the communications components are contained in the device so that a user does not require a separate device such as a smart phone 606. However, this embodiment may still permit the use of a smart phone 606 in conjunction with the smart bolus device 602 for the transmission of some data, such as for example to acquire simple reminders and transmit emergency data. As used herein, the term "smart phone" refers to mobile devices with modern processors, communications components, and user interfaces, and includes the ability to run customized programs or "apps". If glucose monitoring functions are not build into the smart bolus injector, then the device further includes communications components to communicate with a separate glucose monitoring device, such as a CGM device 608 or a BGM (not shown). The CGM 608 or BGM may be hardwired or wirelessly connected to the smart bolus device 602.

In accordance with an illustrative embodiment, the smart bolus device 602 is in continuous, near continuous, or regular communication with one or more external devices such as the smart phone 606, the CGM device 608, or the BGM. The device is programmed to determine an insulin dose based on patient information, and to facilitate auto-dosing. Auto-dosing includes priming, performing a bolus injection, data recording and transmission to a secure site for data management. The patient information can include exercise information, sleep information, diet information, weight information, and other medicines used information. The data recorded preferably includes both glucose concentration data and insulin injection data performed by the bolus injector. An Organic Light-Emitting Diode (OLED) display is preferred due to the ability to present clear images and text lines without a backlight, and to scroll in the horizontal and vertical directions. A scrolling display is preferred to improve user navigation through the menu to customize data and to determine an insulin dose prior to injection. The scrolling display also is preferred for transferring post injection data. OLED displays are preferable in systems for diabetes patients and other patients who may have difficulty with vision.

Figure 6:
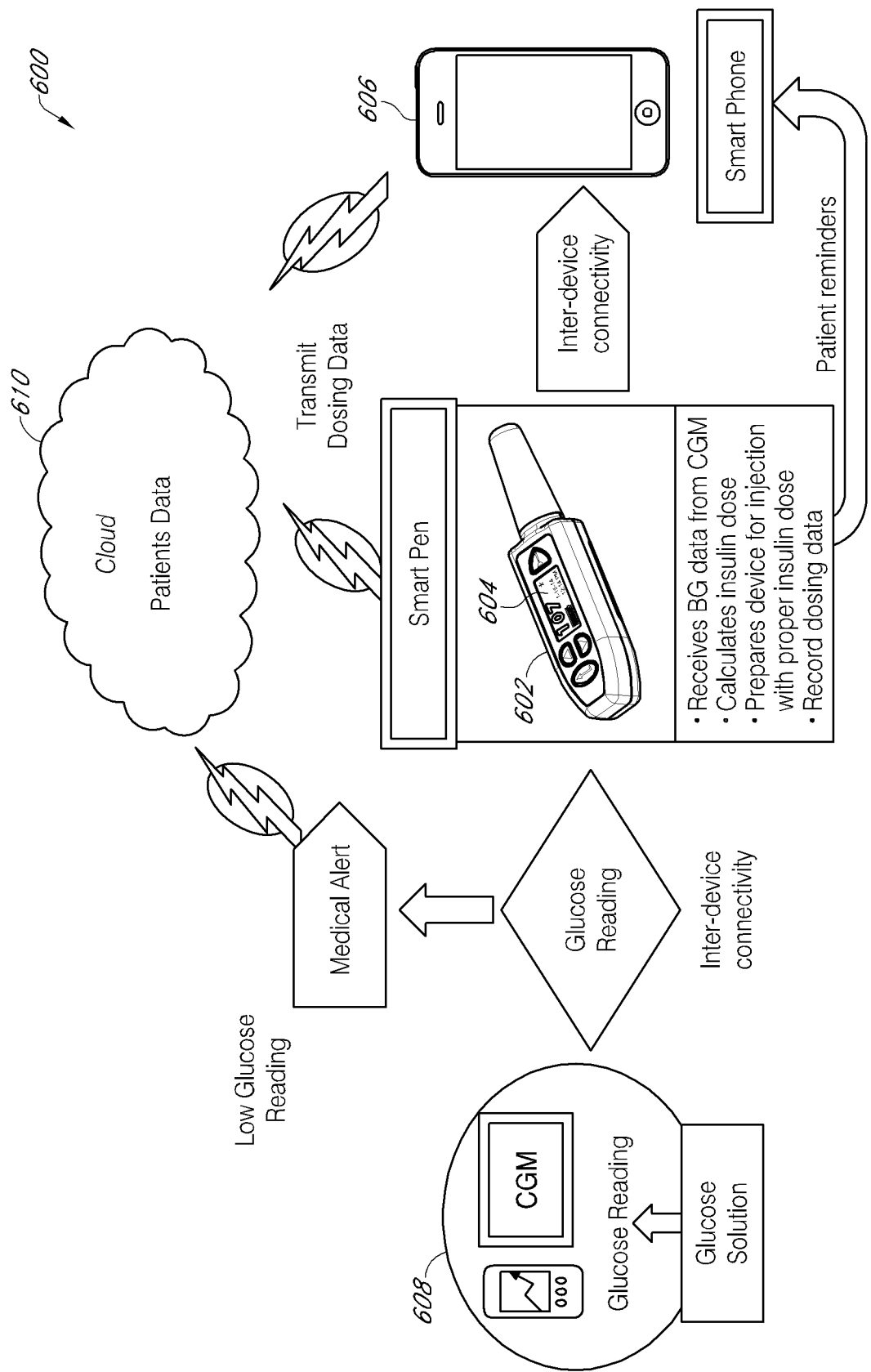
FIG. 6 illustrates a system including a health management access point according to another exemplary embodiment of the invention.

The system 600 of FIG. 6 is smart bolus device 602 centric where the pen is equipped with smart functions to communicate with other devices, determine and prepare injection dose and subsequently sends the info to a secure cloud 610. Smart phone 606 is only needed for reminders and other simple communication tasks. The system 600 is preferable for patients who prefer to minimize dependence on a smart phone.

Figure 7:
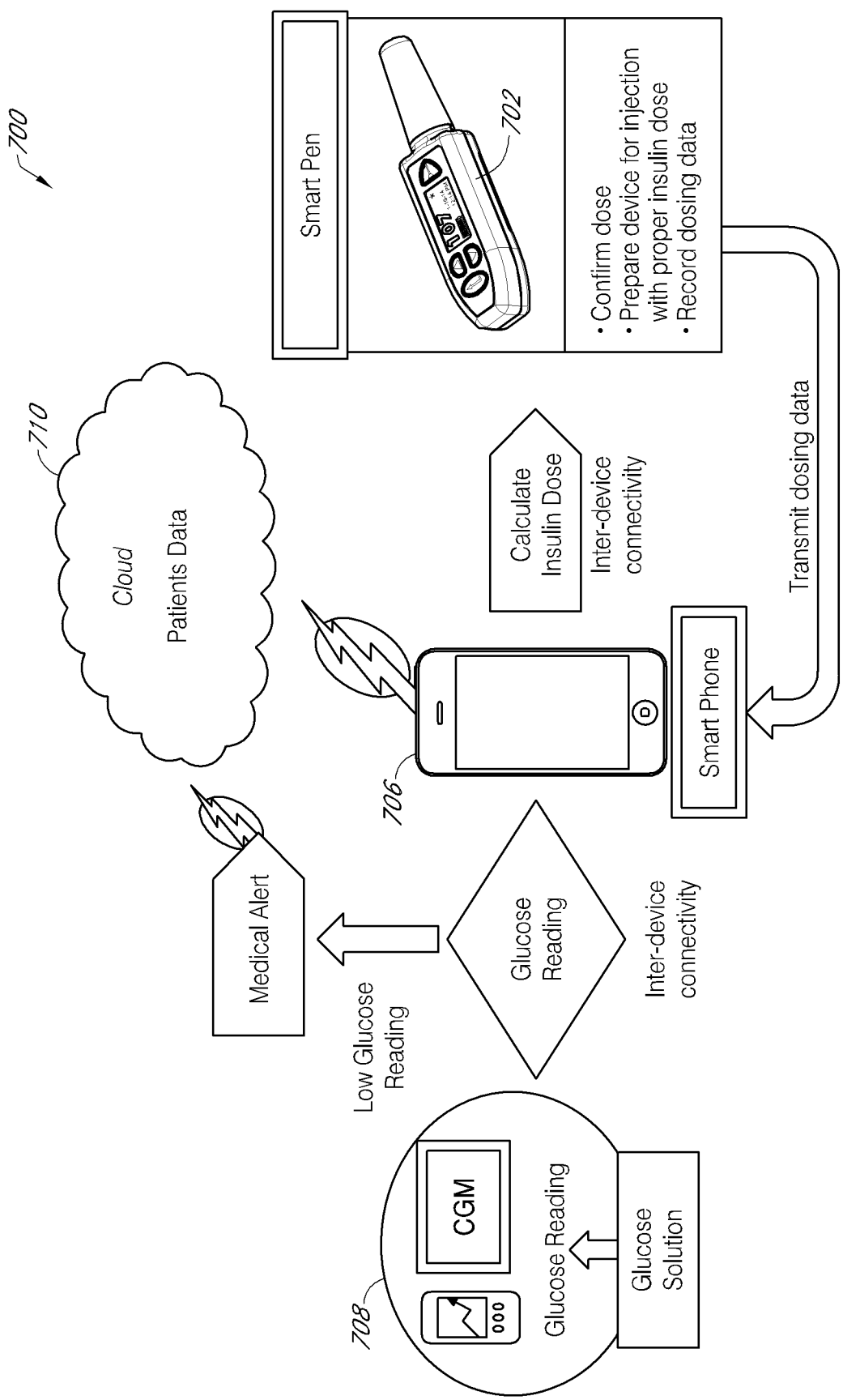
FIG. 7 illustrates a system including a health management access point according to another exemplary embodiment of the invention.

An exemplary system 700 that is smart phone centric will now be described in connection with FIG. 7. In this embodiment the primary function of the bolus device 702 is to facilitate proper insulin injection. The bolus device 702 offers basic safety and smart injection functions. The features to perform the increasingly complex determinations and means to interact with patients, healthcare providers and payers are located on a mobile device such as a smart phone 706 and in the cloud 710. Smart phones have the ability to receive glucose readings from a CGM 708 or a BGM (not shown). The CGM 708 or BGM may be hardwired or wirelessly connected to a smart phone. In some embodiments, the smart phone is in continuous, near continuous, or regular communication with the CGM 708 or BGM. The smart phone 706 determines the required insulin dose based on patient information and feedback, and then transmits the data to the bolus device 702 in order to program an injection.

The smartphone 706 may be in continuous, near continuous, or regular communication with the bolus device 702. After receiving the determined insulin dose information from the smart phone 706, the bolus device 702 prepares the device for injection followed by helping the user to perform self-injection that preferably entails both priming and bolus injection. The bolus device 702 also preferably transfers the successful insulin dose injection data along with a time stamp back to the smart phone 706. The smart phone 706 in turn relays the data to a secure cloud site 710 for data management and access by the patient, their healthcare provider, or any other interested and authorized party. This embodiment may be less expensive and easier to adopt by patients who already carry a smart phone since some of the components, including memory, processor, communications, and application layer, need not be built into the bolus injector device.

The system 700 is smart phone centric where substantially all of the communication apps and patient processes are located. Smart phone 706 communicates with the CGM 708 and receives the blood glucose data. Based on that information, smart phone 706 determines the required insulin dose and sends it to the bolus device 702. The smart phone 706 may also receive information related to exercise, diet, sleep, weight, and other medicines taken through an input from the user or from one or more devices or applications. The required insulin dose information can be based in part on the exercise, diet, sleep, weight, and medication information. Bolus device 702 prepares the injection device with the determined dose for auto dosing by the patient. Bolus device 702 also communicates the injection data (such as successful or incomplete injection) back to the smart phone 706. The smart phone 706 will send the info to the cloud server 710 where it can be accessed by multiple stake holders (patient, relatives, health care provider, insurance, and so on).

One embodiment integrates with a Glucose Binding Protein-Based Continuous Glucose Monitoring (GBP CGM) to provide a less invasive alternative as compared to an insulin pump combined with a Glucose Oxidase based CGM or a smart pen used together with an episodic capillary blood glucose monitor (BGM).

Embodiments of the present invention are advantageous for patients who are on a premixed formulation of short acting and long acting insulin to control their diabetes. Roughly 30% of patients in the U.S. and over 70% of patients in China currently use premixed insulin that is a combination of short and long acting. One difficulty with premixed formulations of insulin is that the patient is required to mix the insulin properly prior to each injection. By integrating the premix insulin injection with an enhanced monitoring and improved delivery method, the smart bolus delivery system could improve therapeutic efficacy, reduce the risk of hypoglycemia, and improve patient treatment outcome.

An embodiment of invention smart injection device preferably includes two features. The first is electronics and connectivity to acquire glucose data, either by a wireless or wired connection, from designated sources including monitoring devices. The designated sources can include CGM's, BGM's, or smart phones. The designated sources may also include devices for monitoring exercise, sleep, diet, weight, and other medication used. In some embodiments, the smart injection device is in continuous, near continuous, or regular communication with one or more of the designated sources. The second feature is automation technology to (a) determine an insulin dose amount by using a bolus calculator, or receive a determined insulin dose from another source, such as a smart phone, (b) mechanical and electronic mechanisms to prepare the device to perform an auto injection, and (c) electronics and connectivity to communicate time-stamped data, including glucose concentration and insulin injection information to a secure database management system where various groups of stakeholders such as patients, healthcare providers and payers may have access to the data.

The cornerstone of good diabetes management is education that facilitates changes in behavior to help improve glucose control and other health outcomes. Unfortunately, many patients often receive minimal instructional information, if any at all, about how to manage their diabetes. Patients need ongoing reinforcement of key concepts and behaviors. Without this ongoing reinforcement, therapy adherence has been shown to decline, healthy living behaviors cease, and complications increase, leading to expensive care and interventions. In order to improve patient education regarding diabetes management, an exemplary embodiment of the present invention preferably includes a number of additional features that will now be described.

First, the system covers key elements of good diabetes management and complication prevention. The focus is on reinforcing education around injection technique current, future infusion sites, and glucose control to lower A1c. More specifically, the system shows patient how to acquire physiological data, determines insulin dose requirements, sets the bolus injector to deliver a dose by priming and delivering a bolus injection, and records data related to glucose concentration measured by the glucose monitor and insulin injected by the bolus injector.

Second, the system helps diabetics to identify and analyze trends on how their blood glucose reacts to their therapy. The system enables patients to communicate therapy doses to other devices, and to capture data from a CGM/BGM and insulin delivery devices. The system preferably provides for overall data management for use by the patient, their healthcare provider and other interested and authorized parties.

Third, the system provides a manual mode for when the smart features of the system are non-functional. If the system integrates with a smart phone, then the system preferably provides behavior reinforcement via the smart phone for patients and healthcare providers on how to handle an emergency situation when the smart delivery system is not functional and needs to go to the manual mode.

Fourth, the mobile education method of embodiments of the present invention ensures that the information is current, timely and customizable.

Fifth, the number of diabetes drugs, both oral and injectable, is expanding along with new drugs and new formulations of existing drugs. This may lead to potential confusion and safety risks. Insurers and healthcare providers are increasingly interested in gaining a better understanding of patient drug behavior, including adherence, compliance, and so on. The present embodiment provides a way to help diabetics capture, store, and report information about drug use, including identifying which drug is being used, how much drug is being infused, when the drug is being infused, and other relevant factors. This information may be used by the patient to ensure proper use and safety. Moreover, the information may form part of a care information ecosystem feeding processes and reporting systems.

Sixth, for patients with type 2 diabetes who are using insulin with other medicaments, the smart delivery system has the capability to send multiple daily messages to facilitate diabetes management. For example, patients with insulin resistance using Byetta via a pre-filled pen injector may be instructed to take their injections twice daily, and to take an Actose medication pill at the appropriate times. This regimen used together with proper diet and exercise helps control blood sugar in adults. Accordingly, the smart phone application portion of the system can provide necessary alerts to the user to improve their compliance with their healthcare providers designated regimen.

Systems according to an exemplary embodiment of the invention advantageously have the delivery accuracy above 97% when performed in open air of highly expensive insulin infusion pumps with the low cost associate with small battery powered 12 mm gear motors used with optical encoders. In addition, systems according to an exemplary embodiment of the invention advantageously generate over 160 psi pressure to meet the requirements of intradermal injection.

While certain exemplary embodiments of the present invention have been shown and described herein with reference to certain preferred embodiments thereof, it will be understood by those skilled in the art that various changes in form and details may be made therein without departing from the spirit and scope of the invention.

What is claimed is:

1. An electronic delivery device for delivering a bolus of medicament to a patient, comprising:
    a medicament cartridge;
    a needle at a distal end of the medicament cartridge;
    a receiver configured to receive patient information from one or more external devices;
    a processor configured to read the received patient information and determine an appropriate bolus dose for the patient;
    a dose setting mechanism configured to set a medicament delivery amount corresponding to the determined bolus dose; and
    a housing having at least one user interface button corresponding to a dispense function for dispensing the determined bolus dose.

2. The device of claim 1, wherein the delivery device is configured to prime the cartridge and needle based on the determined bolus dose.

3. The device of claim 2, wherein the delivery device is configured to initiate a notification that the delivery device is prepared for injection after priming of the cartridge and needle.

4. The device of claim 1, wherein the dispense function comprises a motor connected to a displacement gear.

5. The device of claim 4, wherein the device further comprises an encoder in connection with the motor, and a sensor adapted to sense movement of the encoder and to provide signals indicative of encoder movement to a controller of the delivery device, wherein said controller is adapted to control the bolus amount based on the signals received from the encoder.

6. The device of claim 4, wherein the motor is adapted to prime the cartridge and needle prior to delivery of the bolus.

7. The device of claim 1, further comprising a memory for storing the received patient information from the one or more external devices.

8. The device of claim 7, wherein the processor is programmed to read the patient information from the memory to determine medicament delivery information comprising delivery success status, dose amount, and time of medicament delivery.

9. The device of claim 1, further comprising a blood glucose monitoring sensor and blood glucose monitoring test strip, wherein the blood glucose monitoring sensor is configured to measure blood glucose from the blood glucose monitoring test strip.

10. The device of claim 9, wherein the processor is configured to determine the appropriate bolus dose for the patient based on the measured blood glucose.

11. A method in an electronic delivery device for delivering medicament to a patient, comprising:
    receiving patient information from one or more external devices;
    setting a bolus dosage amount based on the patient information;
    activating a user interface on the delivery device to display the bolus dosage amount; and
    delivering medicament from a cartridge of the delivery device to the patient through a needle.

12. The method of claim 11, further comprising receiving an input on a user interface of the delivery device.

13. The method of claim 11, further comprising measuring blood glucose from a blood glucose monitoring test strip using a blood glucose monitoring sensor within the electronic delivery device.

14. The method of claim 13, wherein setting the bolus dosage amount is based at least partially on the measured blood glucose.

15. The method of claim 11, wherein delivering medicament from the cartridge comprises activating a motor connected to a displacement gear.

16. The method of claim 15, further comprising:
    sensing movement of an encoder in connection with the motor;
    providing signals indicative of encoder movement to a controller of the delivery device; and
    adjusting the bolus dosage amount setting based on the signals received by the controller.

17. The method of claim 15, further comprising setting a medicament priming amount, wherein the motor is adapted to prime the medicament cartridge and needle prior to delivery.

18. The method of claim 11, further comprising:
    storing in a memory the received patient information from the one or more external devices; and
    reading the patient information from the memory and determining medicament delivery information comprising delivery success status, does amount, and time of medicament delivery.

19. The method of claim 11, further comprising priming the cartridge and needle based on the received patient information.

20. The method of claim 19, further comprising initiating a notification that the delivery device is prepared for injection after priming of the cartridge and needle.

21. An electronic delivery device for delivering a bolus of medicament to a patient, comprising:
- a medicament cartridge;
- a needle at a distal end of the medicament cartridge;
- a receiver wirelessly configured to wirelessly connect to one or more external devices, the receiver configured to receive patient information from the one or more external devices; and
- a processor configured to:
  - read the received patient information;
  - determine a patient status based on the received patient information;
  - determine if a notification should be initiated; and
  - initiate a notification.

22. The device of claim 21, further comprising a housing having a user interface configured to display the notification.

23. The device of claim 21, wherein the electronic delivery device is further configured to indicate the notification through auditory, visual, or tactile feedback.

24. The device of claim 21, further comprising a memory for storing the received patient information, wherein the processor is configured to read the patient information from the memory to determine the patient status.

25. The device of claim 21, further comprising a transmitter configured to transmit a notification to an external device.

26. The device of claim 21, wherein the processor is further configured to determine an appropriate bolus dose for the patient, based on the received patient information.

27. The device of claim 26, further comprising a dose setting mechanism configured to set a medicament delivery amount corresponding to the determined bolus dose.

28. The device of claim 21, wherein the delivery device is configured to prime the cartridge and needle based on the received patient information.

29. The device of claim 28, wherein the processor is configured to initiate a notification that the delivery device is prepared for injection after priming of the cartridge and needle.

30. The device of claim 21, further comprising a blood glucose monitoring sensor and blood glucose monitoring test strip, wherein the blood glucose monitoring sensor is configured to measure blood glucose from the blood glucose monitoring test strip.

31. The device of claim 30, wherein the processor is configured to determine an appropriate bolus dose for the patient based on the measured blood glucose.

* * * * *